(12) United States Patent
Serbedzija et al.

(10) Patent No.: US 7,408,095 B2
(45) Date of Patent: Aug. 5, 2008

(54) METHODS FOR INTRODUCING HETEROLOGOUS CELLS INTO FISH TO DETERMINE IF THE HETEROLOGOUS CELLS CONTAIN CANCER CELLS OR A PATHOGEN

(75) Inventors: George N. Serbedzija, Woburn, MA (US); Patricia McGrath, Cambridge, MA (US)

(73) Assignee: Phylonix Pharmaceuticals, Inc., Cambridge, MA (US)

( * ) Notice: Subject to any disclaimer, the term of this patent is extended or adjusted under 35 U.S.C. 154(b) by 489 days.

(21) Appl. No.: 10/766,134

(22) Filed: Jan. 27, 2004

(65) Prior Publication Data

US 2004/0185431 A1 Sep. 23, 2004

Related U.S. Application Data

(62) Division of application No. 09/451,489, filed on Nov. 30, 1999, now Pat. No. 6,761,876.

(60) Provisional application No. 60/110,464, filed on Dec. 1, 1998, provisional application No. 60/100,950, filed on Sep. 18, 1998, provisional application No. 60/075,783, filed on Feb. 22, 1998.

(51) Int. Cl.
*A01K 67/027* (2006.01)
*A61K 49/00* (2006.01)
*A61B 5/00* (2006.01)
*A61B 8/00* (2006.01)
*A61B 10/00* (2006.01)
*C12Q 1/00* (2006.01)
*G01N 33/53* (2006.01)
*G01N 33/574* (2006.01)

(52) U.S. Cl. ............ 800/20; 800/20; 424/9.2; 424/9.1; 424/9.6; 435/4; 435/7.1; 435/7.23

(58) Field of Classification Search .......... 800/20; 424/9.2

See application file for complete search history.

(56) References Cited

U.S. PATENT DOCUMENTS

| 4,220,858 A | 9/1980 | Ikeguchi et al. |
| 4,286,983 A | 9/1981 | Van Gilse et al. |
| 4,816,392 A | 3/1989 | Hokama |
| 4,964,615 A | 10/1990 | Mueller et al. |
| 5,326,692 A | 7/1994 | Brinkley et al. |
| 5,491,084 A | 2/1996 | Chalfie et al. |
| 5,506,208 A | 4/1996 | Eyal et al. |
| 5,510,099 A | 4/1996 | Short et al. |
| 5,565,187 A | 10/1996 | Zikria et al. |
| 5,573,909 A | 11/1996 | Singer et al. |
| 5,658,751 A | 8/1997 | Yue et al. |
| 5,672,470 A | 9/1997 | Hengstenberg et al. |
| 5,681,703 A | 10/1997 | Tomei |
| 5,744,499 A | 4/1998 | Quash et al. |
| 5,932,418 A | 8/1999 | Yager |
| 5,981,218 A | 11/1999 | Rio et al. |
| 2003/0149996 A1 | 8/2003 | Wengler |

FOREIGN PATENT DOCUMENTS

| GB | 2 080 948 A | 2/1982 |
| WO | WO 96/03034 | 2/1996 |
| WO | WO 98/31787 | 7/1998 |
| WO | WO 98/58963 | 12/1998 |

OTHER PUBLICATIONS

Koya, Y et al 2004, Zoological Science, 21:565-573.*
Hatta, K. and Takahashi, Y., "Secondary axis induction by heterospecific organizers in zebrafish," *Dev. Dynamics*, 205:183-195 (1996).
Ho, R. and Kane, D., "Cell-autonomous action of zebrafish *spt-1* mutation in specific mesodermal precursors," *Nature*, 348:20-27 (Dec. 1990).
Sakai, D. K. et al., "Blood type compatibility of lower vertebrates: phylogenetic diversity in blood transfusion between fish species," *Dev. and Comparative Immunol.*, 11:105-115 (1987).
Yang, E. et al., "Norcantharidin inhibits growth of human HepG2 cell-transplanted tumor in nude mice and prolongs host survival," *Cancer Lett.*, 117:93-98 (1997).
Amsterdam et al., "Requirements for green fluorescent protein detection in transgenic zebrafish embryos", Gene, 173: 99-103 (1996).
Armant et al., "Exposure of Embryonic Cells to Alcohol: Contrasting Effects During Preimplantation and Postimplantation Development", Seminars in Perinatology, 20(2): 127-139 (Apr. 1996).
Bakkers et al., "An important developmental role for oligosaccharides during early embryogenesis of cyprinid fish", Pro. Natl. Acad. Sci. USA, 94: 7982-7986 (Jul. 1997).
Baumann et al., "Bipartite Axiation Follows Incomplete Epiboly in Zebrafish Embryos Treated With Chemical Teratogens", The Journal of Experimental Zoology, 230: 363-376 (1984).
Bechter et al., "Teratogenicity of arotinoids (retinoids): comparison of the whole embryo culture system with the in vivo mouse model and the limb bud cell culture assay", Teratol. 44: 29A, #P33 (1991).
Becker et al., "Teratogenic Actions of Ethanol in the Mouse: A Minireview", Pharmacol. Biochem. Behav., 55(4): 501-513 (1996).
Birge et al., "Acetaminophen Hepatotoxicity: Correspondence of Selective Protein Arylation in Human and Mouse Liver in Vitro, in Culture, and in Vivo", Toxicol. Applied Pharmacol., 105: 472-482 (1990).
Boehm, et al., "Antiangiogenic therapy of experimental cancer does not induce acquired drug resistance", Nature, 390: 404-407 (1997).
Bonn, "Blocking angiogenesis in diabetic retinopathy", Lancet, 348: 604 (1996).

(Continued)

*Primary Examiner*—Valarie Bartoglio
(74) *Attorney, Agent, or Firm*—Townsend and Townsend and Crew LLP

(57) ABSTRACT

Methods of introducing heterologous cells into fish are provided. After introduction cells remain viable, and in some instances proliferate, for sufficient time to conduct a variety of analyses on the heterologous cells or the fish or both. Such methods are also useful, for example, for diagnosing the presence of small quantities of cancerous cells or pathogens in patient tissue samples.

15 Claims, 8 Drawing Sheets

OTHER PUBLICATIONS

Figure 1:
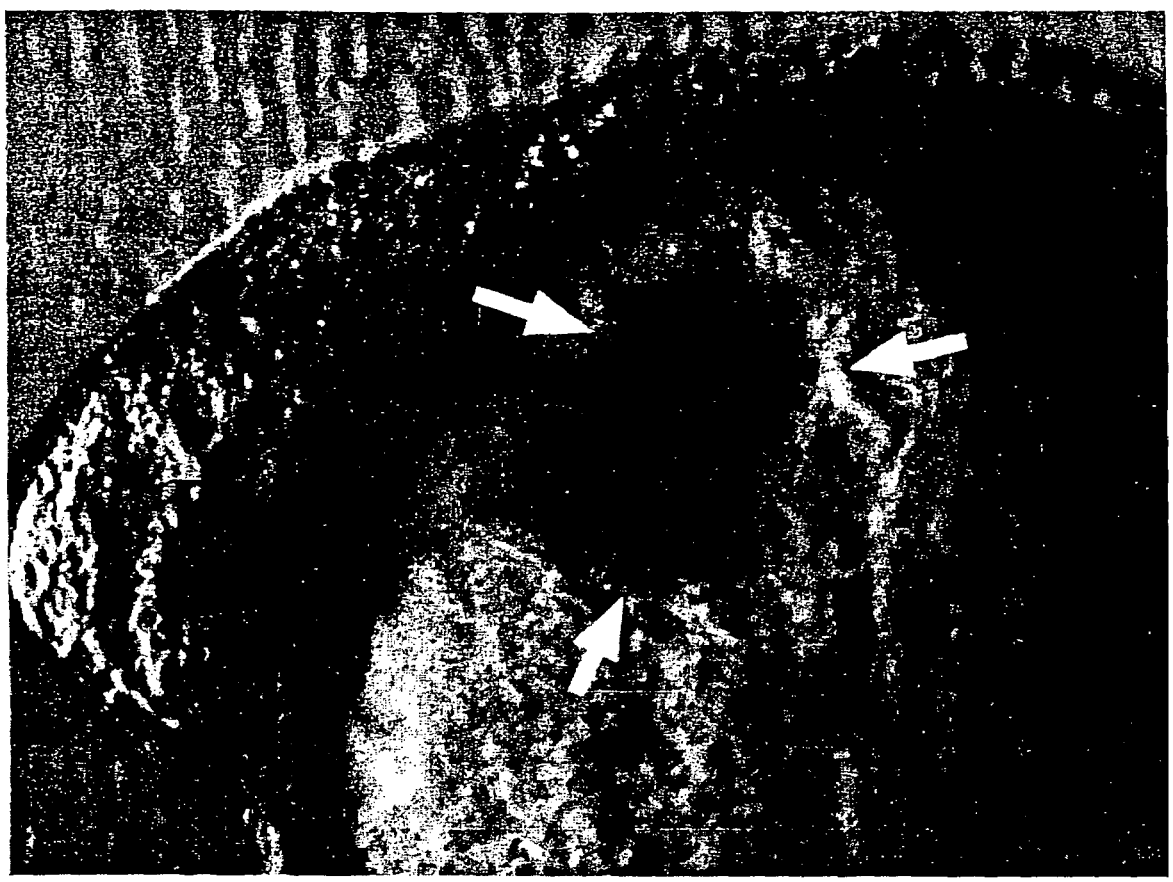

Breier et al., "Angiogenesis in Embryos and Ischemic Diseases", Thromb. Haemost., 78(1): 678-683 (1997).

Bresch,. "Early Life-Stage Test in Zebrafish versus a Growth Test in Rainbow Trout to Evaluate Toxic Effects", Bull. Environ. Contam. Toxicol., 46: 641-648 (1991).

Buchmann et al., "Immunohistochemical Localization of the Cytochrome P450 Isozymes LMC2 and LM4B (P4501A1) in 2,3,7,8-Tetrachlorodibenzo-ρ-dioxin Treated Zebrafish (*Brachyanio rerio*)", Toxicol. Appl. Parmacol. 123: 160-169 (1993).

Chen et al., "Mutations affecting the cardiovascular system and other internal organs in zebrafish", *Development.* 123: 293-302 (1996).

Chatot et al., "Successful Culture of Rat Embryos on Human Serum: Use in the Detection of Teratogens", Science, 207: 1471-1473 (1980).

Chow et al., "The nuclear receptor transcription factor, retinoid-related orphan receptor, regulates retinal progenitor proliferation", Mech. Dev., 77(2): 149-164 (1998).

Cicurel et al., "Post-implantation embryo culture: validation with selected compounds for teratogenicity testing", Xenobiotica, 18(6): 617-624 (1988).

Clarke, "Developmental cell death: morphological diversity and multiple mechanisms", *Anat. Embryol.*, 181: 195-213 (1990).

Collodi et al., "Induction of zebrafish (*Brachydanio rerio*) P450 in vivo and in cell culture", *Xenobiotica*, 24(6): 487-493 (1994).

Couffinhal et al., "Animal Model, Mouse Model of Angiogenesis", *Am. J. Pathol.*, 152(6): 1667-1679 (Jun. 1998).

Dawson, "Additive Incidence of Developmental Malformation for *Xenopus* Embryos Exposed to a Mixture of Ten Aliphatic Carboxylic Acids", Teratology, 44: 531-546 (1991).

Debus et al., "Nematode Test to Estimate the Hazard Potential of Solved Contaminations", Chemosphere, 29(3): 611-621 (1994).

Drake et al., "Exogenous vascular endothelial growth factor induces malformed and hyperfused vessels during embryonic neovascularization", *Proc. Natl. Acad. Sci. U.S.A.*, 92: 7657-7661 (Aug. 1995).

Driever et al., "Zebrafish: genetic tools for studying vertebrate development," TIG, 10(5): 152-159 (1994).

Dubois et al., "DNA adducts and P450 induction in human, rat and avian liver cells after exposure to polychlorobiphenyls", *Mutation Res.*, 345: 181-190 (1995).

Dumont et al., "Vascularization of the Mose Embryo: A Study of *flk-1, tek, tie*, and Vascular Endothelial Growth Factor Expression During Development", *Development Dynamics*, 203: 80-92 (1995).

Eisses, "Teratogenicity and Toxicity of Ethylene Glycol Monomethyl Ether (2-Methoxyethanol) in *Drosophila melanogaster*. Involvment of Alcohol Dehydrogenase Activity", *Teratog. Carcinog. Mutagen.*, 9: 315-325 (1989).

Ellies et al., "Specific craniofacial cartilage dysmorphogenesis coincides with a loss of *dix* gene expression in retinoic acid-treated zebrafish embryos", *Mechanisms of Development*, 61: 23-36 (1997).

Ensenbach et al., "Toxicity of Complex Chemical Mixtures: Acute and Long-Term Effects on Different Life Stages of Zebrafish (*Brachydanio rerio*)", *Ecotoxicology and Environmental Safety*, 30:151-157 (1995).

Feucht et al., "VEGF Induces Cardiovasuclar Malformation and Embryonic Lethality", *Am. J. Pathology*, 151(5):1407-1416 (Nov. 1997).

Folkman, "Clinical Applications of Research on Angiogenesis", *N. Eng. J. Med.*, 333(26): 1757-1763 (Dec. 28, 1995).

Fort et al., "Phase III Interlaboratory Study of Fetax, Part 2: Interlaboratory Validation of an Exogenous Metabolic Activation System for Frogg Embryo Teratogenesis Assay-Xenopus (Fetax)", *Drug and Chem. Toxicol.*, 21(1): 1-14 (1998).

Fouquet et al., "Vessel Patterning in the Embryo of the Zebrafish: Guidance by Notochord", *Developmental Biology*, 183: 37-48 (1997).

Frank et al., "Residues of Insecticides, Fungicides, and Herbicides on Ontario-Grown Vegetables, 1980-1985", *J. Assoc. Off. Anal. Chem.*, 70(6): 1081-1086 (1987).

Gavrieli et al., "Identification of Programmed Cell Death In Situ via Specific Labeling of Nuclear DNA Fragmentation", *J. Cell Biol.*, 119(3): 493-501 (Nov. 1992).

Granato et al., "Fishing for genes controlling development", *Cur. Op. Gen. Dev.*, 6: 461-468 (1996).

Guest et al., "Evaluation of the rat embryo culture system as a predictive test for human teratogens", *Can. J. Physiol. Pharmacol.*, 72: 57-62 (1994).

Hammerschmidt et al., "Genetic analysis of dorsoventral pattern formation in the zebrafish: requirement of a BMP-like ventralizing activity and its dorsal repressor", *Genes and Devel.*, 10: 2452-2461 (1996).

Hanahan, "Signaling Vascular Morphogenesis and Maintenance", *Science*, 277: 48-50 (Jul. 4, 1997).

Heller et al., "Discovery and analysis of inflammatory disease-related genes using cDNA microarrays", *Proc. Natl. Acad. Sci. USA*, 94: 2150-2155 (Mar. 1997).

Herbst et al, "Differential Effects of Laminin, Intact Type IV Collagen, and Specific Domains of Type IV Collagen on Endothelial Cell Adhesion and Migration", *J. Cell Biol.*, 106: 1365-1373 (Apr. 1988).

Hetts, "To Die or Not to Die: An Overview of Apoptosis and its Role in Disease", *JAMA*, 279(4): 300-307 (Jan. 28, 1998).

Hitchcock et al., "Investigations Into Using the Nematode *Caenorhabditis elegans* for Municipal and Industrial Wastewater Toxicity Testing", *Arch. Environ. Contam. Toxicol.*, 33: 252-260 (1997).

Hunt et al., "A distinct Hox code for the branchial region of the vertebrate head", *Nature*, 353: 861-864 (Oct. 31, 1991).

Iida et al., "Suppression of arachidonic acid cascade-mediated apoptosis in aflatoxin B1-induced rat hepatoma cells by glucocorticoids" *Carcinogenesis*, 19(7): 1191-1202 (1998).

Jain et al., "Quantitative angiogenesis assays: Progress and problems", *Nat. Med.*, 3(11): 1203-1208 (Nov. 1997).

Kallman et al. "Genetics of Tissue Transplantation in Isolated Platyrfish Populations", Copeia, 1964, pp. 512-522.

Kerbel, "A cancer therapy resistant to resistance", *Nature*, 390: 335-336 (Nov. 27, 1997).

Kerr et al., "Apoptosis: A Basic Biological Phenomenon With Wide-Ranging Implications in Tissue Kinetics", *Br. J. Cancer*, 26: 239-257 (1972).

Kim et al., "Requirement for Specific Proteases in Cancer Cell Intravasation as Revealed by a Novel Semiquantitative PCR-Based Assay," *Cell* 94:353-362 (Aug. 7, 1998).

Knight, "Adverse Drug Reactions in Neonates", *J. Clin. Pharmacol*, 34: 128-135 (1994).

Law et al., "Hepatotoxicity of the drinking water disinfection by-product, dichloroacetic acid, in the medaka small fish model", *Toxicol. Letters*, 94: 19-27 (1998).

Liao et al., "The zebrafish gene *cloche* acts upstream of a *flk-1* homologue to regulate endothelial cell differentiation", *Development*, 124: 381-389 (1997).

Liepins et al., "Cell Injury and Apoptosis", *Scanning Microscopy*, 8(3): 631-643 (1994).

Long et al., "*GATA-1* expression pattern can be recapitulated in living transgenic zebrafish using GFP reporter gene", *Development*, 124: 4105-4111 (1997).

Losordo et al., "Gerie Therapy for Myocardial Angiogenesis: Initial Clinical Results With Direct Myocardial Injection of phVEGF$_{165}$ as Sole Therapy for Myocardial Ischemia", *Circulation*, 98: 2800-2804 (1998).

Marret et al., "Caffeine-Induced disturbances of early neurogenesis in whole mouse embryo cultures", *Brain Research*, 773: 213-216 (1997).

McDanell et al., "Effect of Dietary Fat on the In Vitro Hepatotoxicity of Paracetamol", *Biochemical Pharmacology*, 44(7): 1303-1306 (1992).

Mizell et al., "The aquatic vertebrate embryo as a sentinal for toxins: zebrafish embryo dechorionation and perivitelline space microinjection", *Int. J. Dev. Biol.*, 41: 411-423 (1997).

Monteith et al., "Comparison of Tacrine-Induced Cytotoxicity in Primary Cultures of Rat, Mouse, Monkey, Dog, Rabbit, and Human Hepatocytes", *Drug and Chem. Toxicol.*, 19(1&2): 59-70 (1996).

Muller et al., "Effect of Concentration on the Cytotoxic Mechanism of Doxorubicin-Apoptosis and Oxidative DNA Damage", *Biochem. Biophys. Res. Comm.*, 230(2): 254-257 (1997).

Mundles et al., "Two in Situ Labeling Techniques Reveal Different Patterns of DNA Fragmentation during Spontaneous Apoptosis In Vivo and Induced Apoptosis in Vitro", *Anticancer Res.*, 15:1895-1904 (1995).

O'Reilly et al., "Endostatin: An Endogenous Inhibitor of Angiogenesis and Tumor Growth", *Cell*, 88:277-285 (Jan. 24, 1997).

Ozato et al., "Production of transgenic fish: Introduction and expression of chicken -crystallin gene in medaka embryos," *Cell Differentiation*, 19:237-244 (1986).

Relou et al., "Effect of culture conditions on endothelial cell growth and responsiveness", *Tissue & Cell*, 30(5): 525-530 (1998).

Rivard et al., "Age-Dependent Impairment of Angiogenesis", *Circulation*, 99: 111-120 (1999).

Roebuck et al., "A Review of the Neuroanatomical Findings in Children with Fetal Alcohol Syndrome or Prenatal Exposure to Alcohol", *Alcoholism: Clin. Exper. Res.*, 22(2): 339-344 (Apr. 1998).

Serbedzija et al., "Regulation in the heart field of zebrafish", *Development*, 125: 1095-1101 (1998).

Serbedzija et al., "Analysis of Neural Crest Cell Migration in Splotch Mice Using a Neural Crest-Specific LacZ Reporter", *Developmental Biology*, 185: 139-147 (1997).

Serbedzija et al., "Cell Death in the CNS of the Wnt-1 Mutant Mouse", *J. Neurobio.*, 31(3): 275-282 (1996).

Serbedzija et al., "Vital dye analysis of cranial neural crest cell migration in the mouse embryo", *Development*, 116: 297-307 (1992).

Serbedzija et al., "Development potential of trunk neural crest cells in the mouse", *Development*, 120: 1709-1718 (1994).

Semino et al., "Synthesis of 'Nod'-like chitin oligosaccharides by the *Xenopus* development protein DG42", *Proc. Natl. Acad. Sci. USA*, 92: 3498-3501 (Apr. 1995).

Semino et al., "Expression of *Rhizobium* Chitin Oligosaccharide Fucosyltransferase in Zebrafish Embryos Disrupts Normal Development", *Annuls New York Academy of Sciences*, 842: 49-54 (1998).

Semino, C. et al., "Homologs of the *Xenopus* developmental gene *DG-42* are present in zebrafish and mouse and are involved in the synthesis of Nod-like chitin oligasaccharides during early embryogenesis", *Proc. Natl. Acad. Sci. USA*, 93: 4548-4553 (May 1996).

Singer, "Sensitive Fluorescent Stains for Detecting Nucleic Acids in Gels and Solutions", *Biotechnol. Intl.*, 1: 267-276 (1997).

Stainier et al., "Mutations affecting the formation and function of the cardiovascular system in the zebrafish embyro", *Development*, 123: 285-292 (1996).

Stainier et al., "The Zebrafish as a Model System to Study Cardiovascular Development", *Trends Cardiovasc. Med.*, 4(5): 207-212 (1994).

Steller, "Mechanims and Genes of Cellular Suicide", *Science*, 267: 1445-1449 (Mar. 10, 1995).

Stringer et al., "Rapid Measurement of Toxicity Using Electrochromic Dyes and Frog Embryos", *Bull. Environ. Contam. Toxicol.*, 51: 557-563 (1993).

Thompson, C.B., "Apoptosis in the Pathogenesis and Treatment of Disease", *Science*, 267: 1456-1462 (Mar. 10, 1995).

Thompson, M.A. et al., "The *cloche* and *spadetail* Genes Differentially Affect Hematopoiesis and Vasculogenesis", *Dev. Biol.*, 197: 248-269 (1998).

Turk et al., "Synthetic Analogues of TNP-470 and Ovalicin Reveal a Common Molecular Basis for Inhibition of Angiogenesis and Immunosuppression", *Bioorganic & Medicinal Chemistry*, 6: 1163-1169 (1998).

Ungvary et al., "Combined Embryotoxic Action of Toluene, a Widely Used Industrial Chemical, and Acetylsalicylic Acid (Aspirin)", *Teratology*, 27: 261-269 (1983).

Van Leeuwen et al., "Fish Embryos as Teratogenicity Screens: A Comparison of Embryotoxicity between Fish and Birds", *Ecotoxicol. Environ. Safety*, 20: 42-52 (1990).

Weinstein et al., "*gridlock*, a localized heritable vascular patterning defect in the zebrafish", *Nature Med.*, 1(11): 1143-1147 (Nov. 1995).

Westerfield, *The Zebrafish Book: A Guide for the Laboratory Use of Zebrafish (Danio rerio)*, 3d edition, (1993).

Wylie, Zebrafish Issue, Title page and Table of Contents, *i-ii*, *Development*, 123: 1-481 (1996).

Wolff et al., "Dexamethasone Increasing Hepatotoxicity of MTX in Children with Brain Tumors," *Anticancer Res.*, 18: 2895-2900 (1998).

Zetter, "Angiogenesis and Tumor Metastasis", *Annual Rev. Med.*, 49: 407-424 (1998).

* cited by examiner

METHODS FOR INTRODUCING HETEROLOGOUS CELLS INTO FISH TO DETERMINE IF THE HETEROLOGOUS CELLS CONTAIN CANCER CELLS OR A PATHOGEN

CROSS-REFERENCE TO RELATED APPLICATIONS

This application is a divisional of U.S. application Ser. No. 09/451,489, filed Nov. 30, 1999 and issued as U.S. Pat. No. 6,761,876, which claims of the benefit of U.S. Provisional Application No. 60/110,464, filed Dec. 1, 1998. Commonly owned U.S. Provisional Application No. 60/100,950 filed Sep. 18, 1998, and U.S. application Ser. No. 60/075,783, filed Feb. 22, 1998, are directed to related subject matter. Each of the above applications are incorporated by reference in its entirety for all purposes.

BACKGROUND

Currently, the mouse is the model system of choice for cell transplantation assays (Greiner, et al., 1998). Cells are injected into adolescent or adult mice followed by injection of compounds and examination for viability and tumor size (Yang, et al., 1997; Katsanis et al., 1998). To prevent cell rejection, transplantation of human cells must be performed using immunosuppressed mice from either Nude or SCID mouse lines (Yang, et al., 1997; Greiner, et al., 1998; Katsanis et al., 1998). However, because these mice do not exhibit an immune response, they are less hardy than normal mice and more susceptible to toxic effects of the compounds. In addition, these animals are expensive to develop and maintain. Furthermore, because mice develop en utero, it is not possible to assay mouse embryos, greatly complicating assessment of the effect of compounds on developmental processes. A hollow fiber model, in which tiny tubes filled with tumor cells are implanted into mice in a variety of sites is also used for drug screening. By monitoring the tumor cell killing effects of drugs on the implants, researchers can test which drugs actually make it to the tumor sites when the drugs are administered in different ways: intravenously versus orally, for example.

Limitations of animal models have spurred the NCI and others to also test drug candidates in cultures of human cells and the Institute now relies on a panel of 60 human tumor cell lines, including samples of all the major human malignancies. Drugs to be tested are fed to subsets of the panel, based on tumor cell type and their cell killing activity is monitored.

Clonogenic assays are also performed. In this method, cell lines or a patient's tumor cells are grown in petri dishes or culture flasks and the cell's responses to various anticancer treatments are monitored. However, these assays are also problematic. Sometimes they do not work because the cells simply fail to divide in culture. Furthermore, results do not predict how an anticancer drug will perform in the body.

In a continuing search for faithful models of human carcinogenesis, NCI has recently begun reclassifying the cells based on tissue type-breast cancer versus colon cancer, for example, according to the types of genetic defects the cells carry. To enable drugs that counteract specific defects to be prescribed most effectively, researchers are also developing technologies for analyzing the gene defects in each patients' tumors in order to determine if drugs that correct specific defects can be identified, since they could then be matched to each individual tumor cell makeup.

To create better models of cancer development in humans, investigators are now drawing on the growing knowledge of human cancer related gene mutations. They are genetically altering mice so that they carry the same kinds of changes either abnormal activation of cancer promoting oncogenes or loss of tumor suppressor genes that lead to cancer in humans. The hope is that the mice will develop tumors that behave the same way the human tumors do. One mutant mouse strain, for example lacks a working APC gene, a tumor suppressor that lead to colon cancer when lost or inactivated. So far the results have been mixed.

SUMMARY OF THE CLAIMED INVENTION

The invention provides methods of cellular analysis using fish. Such methods entail introducing one or more heterologous cells into a fish, and analyzing a property of the cells or the fish. The methods are particularly suited for introduction of heterologous cells into fish embryos, particularly zebrafish embryos. Introduced cells remain viable at least until the analyzing step is performed. Some cell types undergo proliferation in the recipient fish. In some methods, the fish is contacted with an agent, and the analyzing determines whether the property is responsive to administration of the agent. Properties of heterologous cells or fish that can be analyzed include differentiation markers, survival of the fish, proliferation of the heterologous cells, movement of the heterologous cells relative to an initial site of introduction, death of heterologous cells or cells of the fish, or proliferation of heterologous cells. In some methods, the heterologous cells are cancer cells. In some methods, the heterologous cells are stem cells. In some methods, the heterologous cells are differentiated cells. In some methods, the heterologous cells are human cells. In some methods, the heterologous cells are bacterial or fungal cells. In some methods, the cells are virally infected cells. Some methods further comprising recovering heterologous cells from recipient fish.

The invention further provides methods of screening an agent for activity against cancerous cells. Such methods entail introducing one or more cancerous cells into a population of fish, administering the agent to the population of fish, and monitoring an effect of the agent on development of the cancerous cells in the population of fish. In some methods, the monitoring step comprises determining an EC50 for the effect of the agent on development of the cancerous cells in the fish. In some methods, the monitoring step comprises detecting an LD50 of the agent on the population of fish. Optionally, the method is repeated for a plurality of agents, and an agent with a low EC50|LD50 ratio is formulated with a carrier as a pharmaceutical composition.

The invention further provides methods of propagating cells. Such methods entail introducing one or more heterologous cells into a fish, culturing the fish under conditions in which the cells proliferate; and recovering the proliferated cells. In some methods, the cells differentiate in the course of proliferation, and the cells are recovered as a differentiated tissue. In some methods, recovered cells are transplanted into a patient, optionally the same patient from whom the heterologous cells were obtained.

The invention further provides methods of diagnosing a sample for a cancerous cell or pathogen. Such methods entail obtaining a sample from a patient containing a population of cells; introducing the population of cells into a fish; and detecting a property of the population of cells to indicate whether the population comprises a cancerous cell or pathogen.

BRIEF DESCRIPTIONS OF THE FIGURES

FIG. 1: Twenty-four hours after transplantation, embryos in which the HepG2 cells were visible as cell masses (arrows) in the yolk (Y). Except for the cell mass, embryos look quite normal. The eye (E) and the otic vesicle (OT)) are labeled for orientation.

Figure 2:
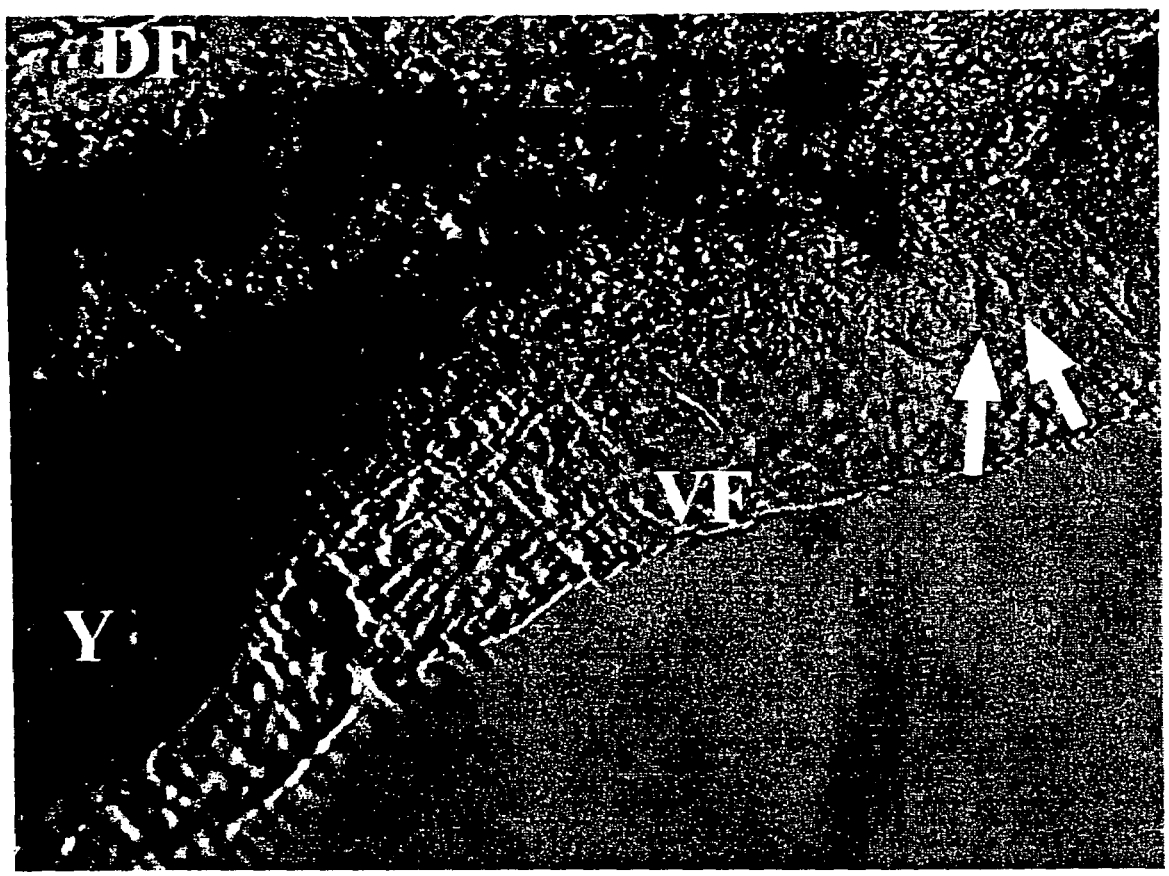

FIG. 2: Forty-eight hours after transplantation, embryos in which the HepG2 cells were visible as individual cells(arrows)in the body. The dorsal fin (DF), ventral fin (VF) and yolk (Y) are labeled for orientation.

Figure 3:
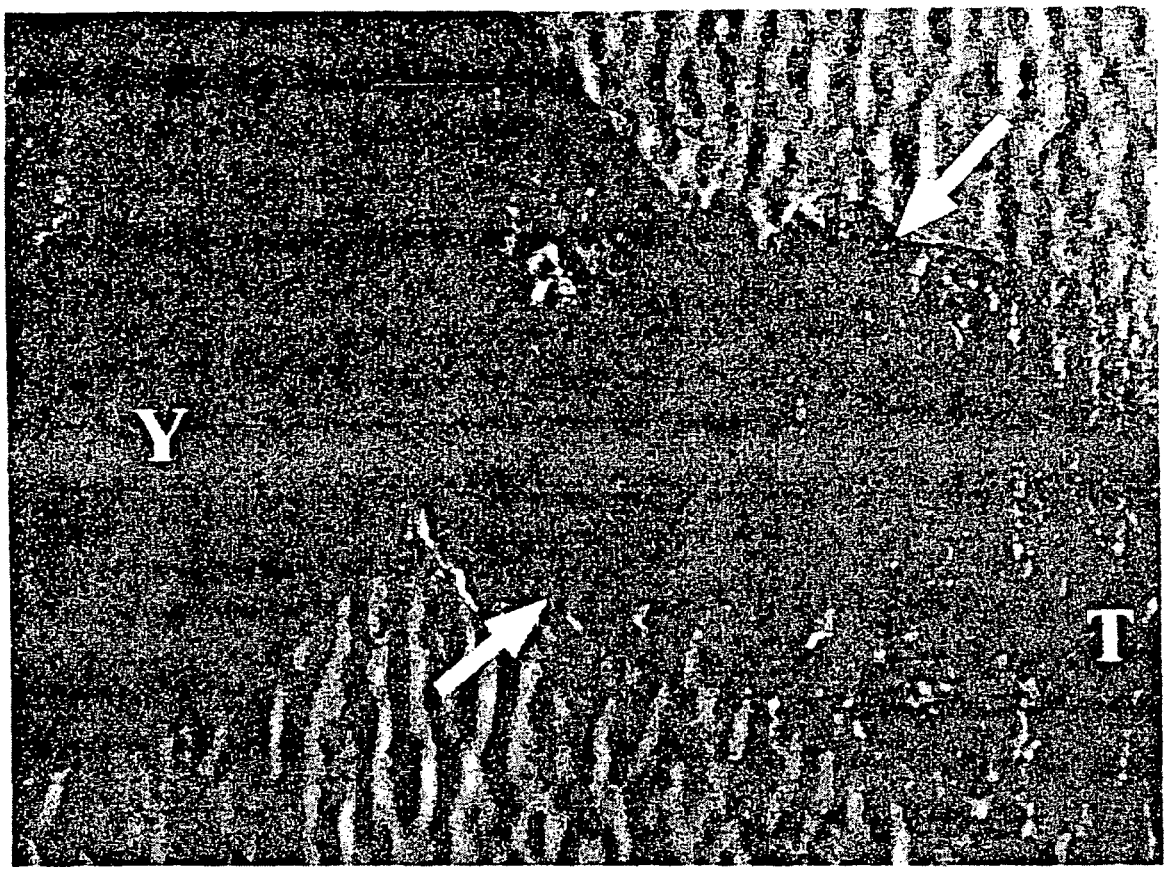

FIG. 3: Twenty-four hours after transplantation, embryos in which the HepG2 cells were visible as a large mass of cells associated with morphological defects (arrow). The tail (T) and the yolk are labeled for orientation.

Figure 4:
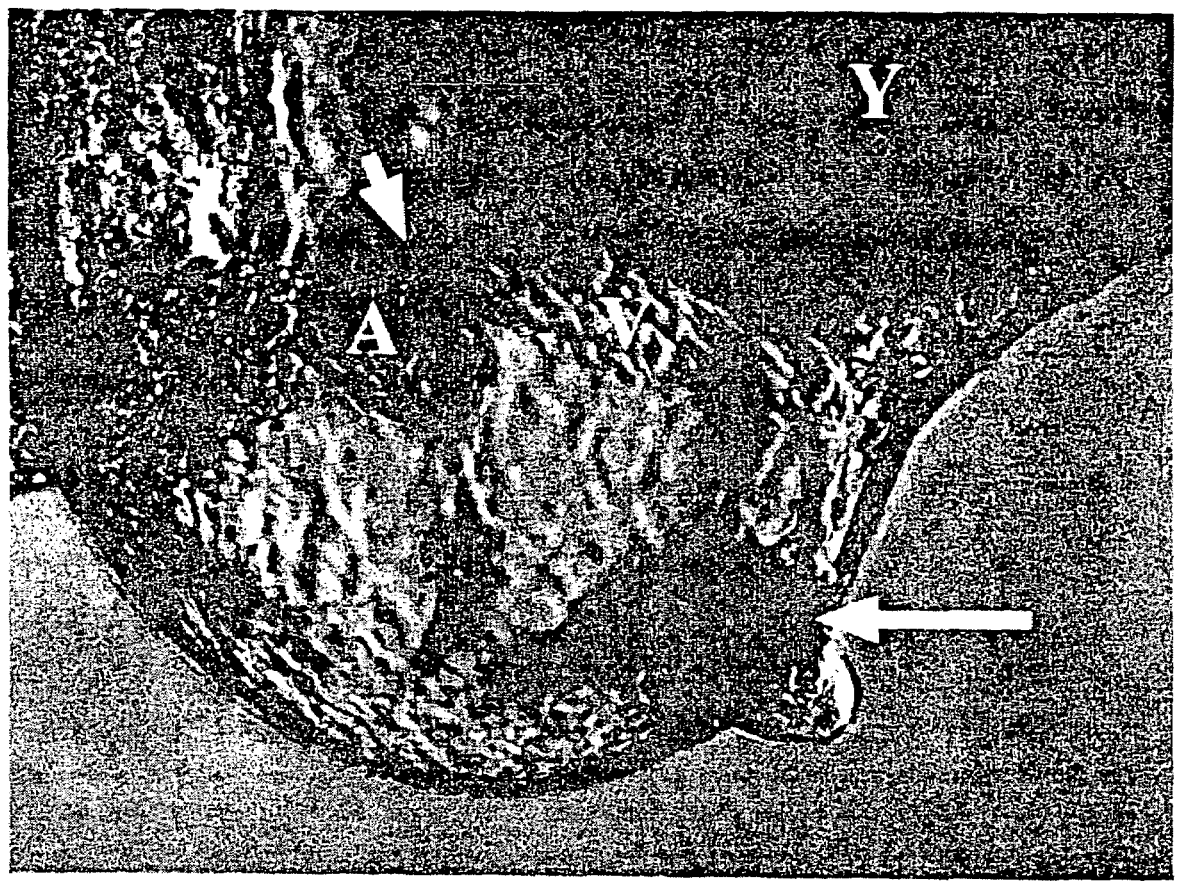

FIG. 4: Forty-eight hours after transplantation, HepG2 cells can be seen as a large mass in the pericardium of the embryo (long arrow). The presence of the HepG2 cells appears to have had a teratogenic effect on the developing heart (short arrow) which is reduced in size and was observed to beat irregularly, most likely cause by the secretion of VEGF from the HepG2 cells. The atrium (A), ventricle (V) and yolk are labeled (Y).

Figure 5:
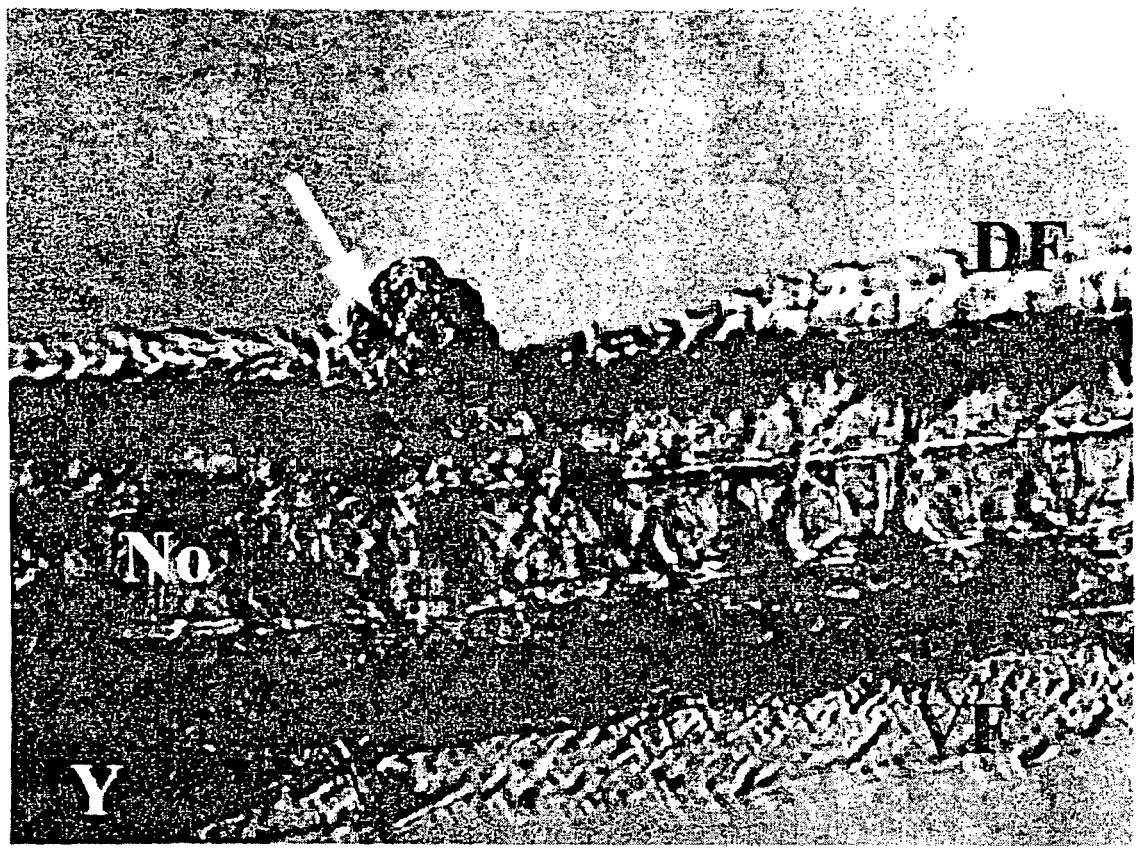

FIG. 5: Forty-eight hours after transplantation, the HepG2 cells are visible as a mass of cells on the dorsal portion of the tail. Zebrafish cells incorporated into the cell mass (arrow). The notochord (No), dorsal fin (DF), ventral fin (VF) and yolk (Y) are labeled for orientation.

Figure 6:
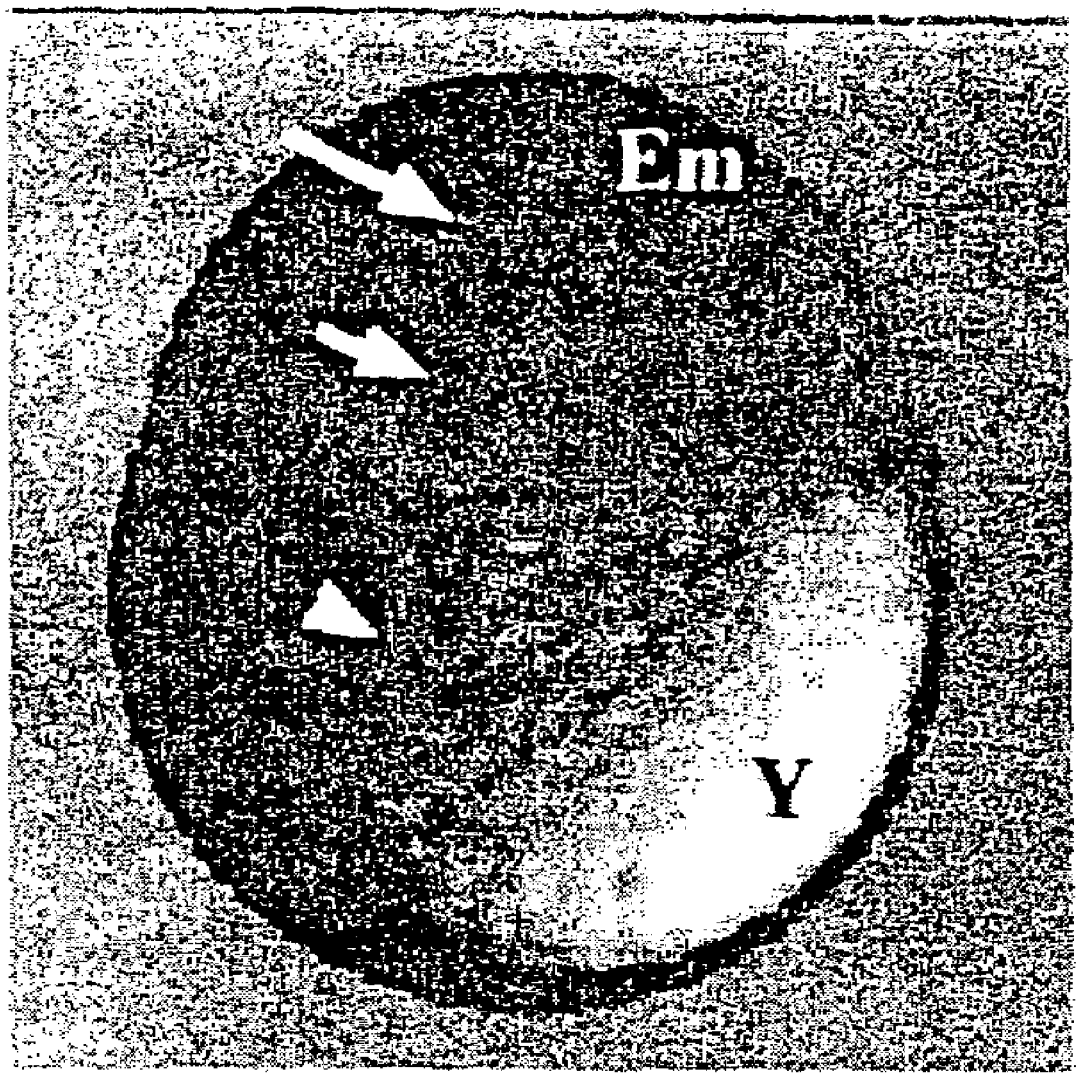

FIG. 6: Transplantations were carried out in three different regions of the high stage embryo: Into the animal portion of the embryo (Em) without a priori knowledge of the position of the transplanted cells in the hosts (long arrow); Into random positions in the yolk cell (Y; arrowhead) and; Into the margin (short arrow) between the embryo and the yolk ball.

Figure 7:
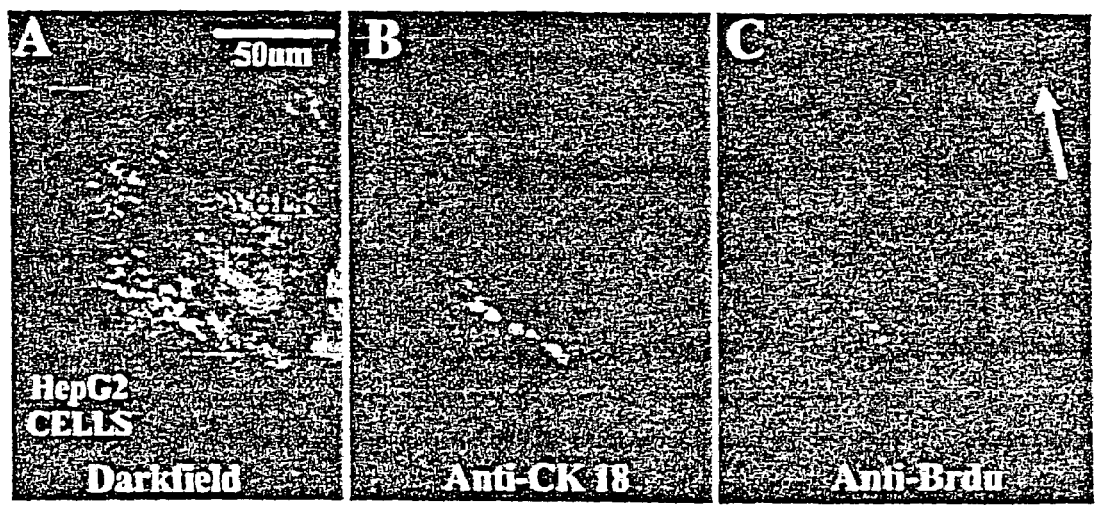

FIG. 7 panels A-C depict BrdU and cK-18 Antibody Staining of HepG2 cells in xenograph embryos 48 hr after transplantation. FIG. 7, panel A: Darkfield image showing the yolk and HepG2 cell mass location; FIG. 7, panel B: Epifluorescence image of the same embryo using a rhodamine filter set indicates localization of CK18 to the cell mass. No CK18 staining was observed in the host tissue or in control embryos. FIG. 7, panel C: Epifluorescence image of the same embryo using a fluorescein filter shows BrdU labelling in the HepG2 cell mass. Because the yolk is spherical most of the Brdu-labelled cells of the yolk syncytial layer are out of focus. The white arrow indicates host cells labelled with BrdU.

Figure 8:
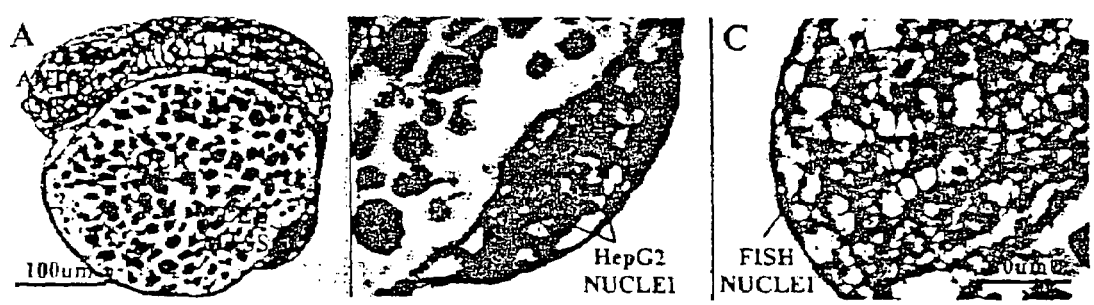
Figure 9:
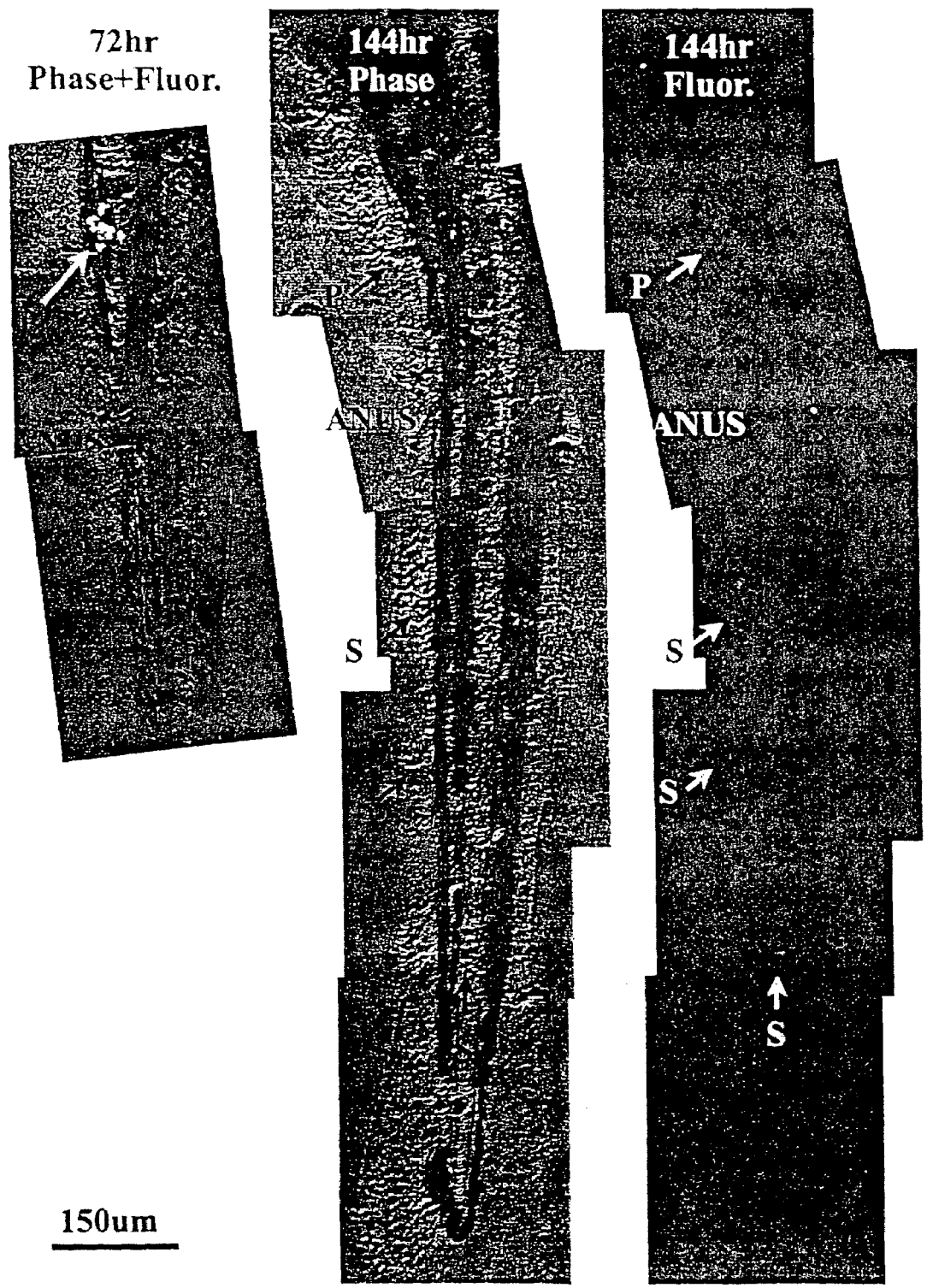

FIG. 8, panels A-C show that transplanted HepG2 cells have tumor cell morphology. FIG. 8, panel A: Brightfield image of a oblique sagittal section though a xenograft embryo. The notochord (NC) and anterior central nervous system (ANT.CNS) are labelled or orientation. FIG. 8, panels B and C: Higher magnification image of the cell mass and the anterior CAN. The nucleic of HepG2 cells are larger and lighter FIG. 9: Satellite cell mass formation in xenograft embryos. Phase and fluorescence images of the same xenograft embryo 72 hr and 144 hr after transplantation. At 72 hr, the cells of the primary mass (P) appeared to disperse. By 144 hours, satellite cells masses (s) visible in both phase and fluorescence, were present throughout the tail of the embryo. For orientation, the anus is labelled.

DEFINITIONS

Stem cells are non-terminally differentiated, can divide without limit, and give rise to progeny, which can continue to divide or can differentiate. Stem cells can be totipotent, pluripotent or unipotent. Totipotent stem cells (e.g., embryonic stem cells) can give rise to every cell type in an adult organism. Pluripotent stem cells can give rise to more than one differentiated cell type. A unipotent stem cell can give rise to a single differentiated cell type. Stem cells are generally characterized by small size, low granularity, low cytoplasmic to nuclear ratio and no expression of osteopontin, collagens and alkaline phosphatase. Stem cells are known for epidermis, intestinal, epithelial and hematopoietic systems. Stem cells for cells of bone, cartilage, fat and three types of muscle (smooth, skeletal and cardiocyte) are thought to a common mesenchymal stem cell precursor (Owen et al., *Ciba Fdn. Symp*. 136, 42-46, 1988); Owen et al., *J. Cell Sci*. 87, 731-738 (1987)).

A set of differentiation markers means one or more phenotypic properties that can be identified and are specific to a particular cell type. Differentiation markers can be transiently exhibited at various stages of cell lineage. Pluripotent stem cells that can regenerate without commitment to a lineage express a set of markers that may be lost when commitment to a cell lineage is made. Precursor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products and receptors.

Some examples of differentiation markers for specific cell types are as follows. Cardiac myosin isozyme expression and the cardiac specific pattern of creatine kinase isozyme expression when identified together on the same cell or a clonal population of cells are markers for cardiac muscles cells. Cardiocytes can also be recognized by their bifurcated appearance by light microscopy and capacity to form gap junctions. Such cells can be recognized by forming an electric potential across confluent cells and detecting transfer of signal across the cells. Muscle α-actin mRNA, and smooth muscle cell actin are differentiation markers of myocytes. Myosin isozyme expression and a muscle-specific pattern of creatine kinase isozyme expression when identified in a cell or clonal population are markers for skeletal muscle cells. Osteoblast cells secrete bone matrix material. ALP, osteocalcin expression, PTH-induced cAMP expression and bone mineralization capacity identified together in a cell or clonal population of cells are markers of differentiation for osteoblasts. Chondrocytes secrete cartilage. Aggrecan and collagen Type IIB identified in a cell or clonal population of cells are markers for chondrocytes. Keratinocytes secrete keratin and can be recognized using commercially available stains. Adipocytes produce lipids and can be recognized by Oil Red 0 staining.

Cells are heterologous to an individual fish if obtained from a different individual. Typically, the different individual is from a species other than fish, for example, from a mammal.

DETAILED DESCRIPTION

I. General

The invention provides methods for introducing heterologous cells into fish for subsequent analysis or recovery. The fish provide an in vivo incubator in which heterologous cells can undergo a number of physiological processes including proliferation, differentiation, expression, secretion, and metastasis. The methods have a number of applications including screening potential drugs for effects on cellular process, propagation of cells for subsequent use in cell therapy or tissue engineering, and diagnosis of patient biopsies for presence of proliferating and/or metastasizing cells. The methods are premised, in part, on the insight that cells from other species, particularly humans, can proliferate in fish notwithstanding differences in body temperature between different species. For example, the human body temperature is ~36° C. while zebrafish normally develop at 27° C. and cannot be raised at temperatures above 32° C. The present application provides evidence that heterologous cells, can nevertheless survive and/or proliferate in fish.

There are several advantages of using fish for transplantation assays relative to laboratory animals such as mice. First, early fish embryos have not yet developed an immune system and are isolated from any effects of the maternal immune system so that heterologous cells are not subject to immune rejection. Second, due to the small size of fish embryos, it is possible to analyze and/or recover a relatively small number of transplanted cells (e.g., 1, 10, or 1000 cells per embryo). Third, some types of fish embryo are relatively transparent facilitating direct microscopic observation of a number of physiological processes with the cells. Fourth, fish embryos can be cultured in solution facilitating contacting heterologous cells with potential drugs.

In general, cells that proliferate in their native environment (e.g., JK cells) also proliferate when transplanted into fish. Cells that are incapable of proliferation in their native environment (e.g., CCL37 lymphoma cells) usually do not proliferate in fish, although in some instances can be induced to proliferate by treatment with appropriate growth factors or other agents. Introduced cells typically remain viable for a period sufficient to conduct various analyses described below (for example, at least an hour and typically at least a day, and sometimes up to three days, a week or longer). Cells that undergo proliferation preferably undergo at least 1, 5 or 10 rounds of doubling as components of the recipient fish. In general, undifferentiated cells undergo differentiation on introduction into fish, whereas terminally differentiated cells remain in that state. Heterologous cells can be obtained from a different species than the recipient fish and are typically obtained from mammals, such as cats, dogs, horses, bovines, mice, rats, rabbits, guinea pigs, primates, and particularly humans; bacteria, plants and birds.

Any type of fish can be used as the recipient for heterologous cells. Examples of suitable fish include teleosts particularly zebrafish, medaka, Giant rerio or puffer fish. Procedures for culturing different types of fish are similar and are described by e.g., *Medaka (killifish): Biology and Strains* (Keigaku Pub. Co., Tokyo, Yamamoto T. ed., 1975) Cells are typically introduced into an embryonic form of the fish. Preferred stages of embryonic development for introduction of cells are the 128 cells stage, the 256 cell stage, the 1 k cell stages, the high stages, characterized by blastodisc perches high on the yolk cells, the oblong cells, at which the animal-vegetal axis of the blastula shortens, with the blastodisc compressing doun on the yolk cell, and the sphere stage, at which continued shortening along the animal-vegetal axis generates a late blastula of smooth an approximately spherical shape. Typically, at least 1, 10, 100, 1000, 10,000, 100,000, 1,000,000 cells are introduced into a recipient fish.

Zebrafish, and particularly zebrafish embryos are a preferred recipient for heterologous cell transplantation. The molecular basis of patterning and development in zebrafish is either identical or similar to man (Chen & Fishman, 1996; Granto and Nusselien-Volhard, 1996, ed Wylie, 1996). Further, because the thymus forms at around 72 hr, by which time the immune system has not yet developed, early zebrafish embryos show good tolerance to heterografts (or xenografts). The tolerance is shown by the fact that homografts are extremely well tolerated in zebrafish, and have been used in transplantation experiments for a number of years. In addition, because the embryo is transparent, internal morphogenic changes, including organ development, metastasis and growth of tumors, and effects of drugs can easily be examined. Since a single mating produces 100-200 externally fertilized eggs, large numbers of embryos can be injected with cells. Chemicals can be added directly to the solution in which the fish swims, permeating the intact embryo, making drug exposure and subsequent examination comparatively straightforward. The zebrafish also offers advantages over other animal models because zebrafish embryos develop more rapidly than do other animal embryos. In general, the body plan, organs, tissues, and other systems of zebrafish develop much more rapidly than do similar components in other vertebrate models (e.g., The mouse). The entire vertebrate body plan of the zebrafish is typically established within 24 hours. A fully functioning cardiovascular system is evident within the first 24 hours of development (Stainier & Fishman, 1994). The remaining organs of the zebrafish, including the gut, liver, kidney, and vasculature, are established within 48 hours. The hatched zebrafish embryo nearly completes morphogenesis within 120 hours, thereby making it highly accessible to manipulation and observation and amendable to high-throughput automated observation and detection procedures.

The zebrafish embryo can survive by diffusion of oxygen from the water and nutrients from the yolk and thus even the absence of the entire circulatory system is well tolerated during early development (Weinstein et al., 1995). Single zebrafish embryos can be maintained in fluid volumes as small as 100 microliters for the first six days of development; consequently, embryos can be kept in culture in individual microtiter wells or multi-well plates. Test compounds can be added directly to the solution in which the fish is immersed. Test compounds added to the zebrafish embryo permeate the intact embryo directly, making this multi-well format particularly attractive for high through-put and automated compound screening.

Since zebrafish are externally fertilized, manipulation of the embryos is comparatively easy. Cell transplantation is carried out by micro-injection, a technique that is well established in the zebrafish (Ho & Kane, 1990; Hammerschmidt et al., 1996). Since a single mating can produce 100-300 embryos, generation of large numbers of heterograft host embryos is relatively straightforward. Furthermore, inbred strains are available and thousands of fish can be raised inexpensively in a small room of aquaria. An important advantage of the potential of zebrafish assays is cost. Currently, the average mouse assay costs about $1630 when performed by the government and $2900 when done commercially. The high cost is due to the high cost of generating and maintaining mice as well as the lack of automation for the highly manual injections and subsequent analysis. In contrast, zebrafish are comparatively cheap to maintain and because the embryos can be placed in individual microtiter wells, automated analysis with standard liquid handling equipment is possible. A comparison of key features of vertebrate model systems follows.

| Comparison Of Vertebrate Model Systems | | | | |
|---|---|---|---|---|
| | monkey | mouse | frog | z-fish |
| In utero gestation | yes | yes | yes | no |
| Embryogenesis | 9 months | 21 days | 1 10 hrs | 72 hrs |
| Embryos per mating | 1 | 8-16 | 100-200 | 100-200 |

-continued

Comparison Of Vertebrate Model Systems

|  | monkey | mouse | frog | z-fish |
|---|---|---|---|---|
| Transparent | no | no | no | yes |
| Microplate analysis | no | no | yes | yes |
| Drug delivery | inject | inject | inj/solution | inj/solution |

II. Agents for Treatment of Cancer

The present methods provide a means for screening agents for toxicity to cancerous cells and/or capacity to inhibit the proliferation and/or metastasis of cancer cells. The methods work by transplanting cancerous cells into one or more fish and administering an agent to be screened. Typically, the cancerous cells are also transplanted into one or more control fish that do not receive agent for purposes of comparison, although historical controls can also be used. The fate of the cancer cells is then monitored in the fish compared with contemporaneous or historical control animals. In the control animals, cancerous cells persist, proliferate and/or metastasize. In treated animals, desirable activity of an agent is manifested by an inhibition of proliferation of cancerous cells, and/or an inhibition of metastasis, and/or complete elimination of cells.

In some methods, the effect of agent on fish cells is also monitored as a measure of side-effects of an agent. The transparent nature of the fish, such as zebrafish, facilities visualization of any perturbations of the agent on development of fish tissues and organs. In addition, the composition and distribution of mRNA and proteins within fish embryos can be monitored by in situ hybridization. Effects of the agent on treated fish can be compared with contemporaneous or historical controls as a measure of side effects of the agent. Ideal agents shows a high ratio of activity against cancerous cells to side effects against fish cells.

1. Agents to be Screened

Agents to be screened for activity against cancer cells or in other types of assay described below, can be from combinatorial libraries of peptides or small molecules, hormones, growth factors, and cytokines, or can be naturally occurring molecules or can be from existing repertoires of chemical compounds synthesized by the pharmaceutical industry. Combinatorial libraries can be produced for many types of compound that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980. Compounds to be screened can also be obtained from the National Cancer Institute's Natural Product Repository, Bethesda, Md. Existing compounds or drugs with known antineoplastic activity can also be screened to determined an activity to side effects profile.

2. Cancerous Cells

Cancerous cells include primary cells obtained from cancerous tissue in humans and other mammals. There are several different cancerous cell types, including leukemias, which affect blood cells, sarcomas, which arise in bone muscle or connective tissue, and carcinomas, which arise in epithelial cells and includes breast, colon, lung cancers, the most common types of cancer. Cancerous cells also include lymphomas, blastomas, gliomas, teratomas, and neurofibromatomas. Cancerous cells also include cell lines that proliferate indefinitely and give rise to tumors in laboratory animals, such as mice. Cancerous cells also include precancerous cells that do not give rise to tumors in laboratory animals, but which bear at least one differentiation marker that distinguishes cancerous cells from normal cells. Precancerous cells are often further characterized by capacity to proliferate indefinitely.

3. Route of Cell Administration

Cancerous and other cells are typically administered to the fish embryos by microinjection. The fish are typically wild-type although mutant strains of fish can also be used for analysis of the interaction between therapeutic agents and specific genetic deficiencies. The fish are typically early-stage embryos but larva or adult zebrafish can also be used. Cells can be injected into either the yolk or body of a fish embryo, or both. Cells can be injected at a single or multiple sites. Fish embryos are typically cultured for a period before administering agent to allow cancerous cells to adapt to the new environment, proliferate and/or metastasize. Any fish not surviving transplantation of cancerous cells can be removed before administration of agent.

4. Administration of Agents

Agents can be administered before, at the same time as, or after introduction of cancerous (or others cells) into fish. Usually, agents are administered after introduction of cancerous cells and following a period sufficient for the cancerous cells to begin proliferation and/or metastasizing in the zebrafish. The interval is typically from 12-36 hr after introducing the cells, preferably about 24 hr after introducing the cells. After administration of agent, fish are cultured for a further period, typically, for at least about 24 hr, and sometimes for 1, 3 or 6 months, or until death. A typically monitoring regime is to monitor every 24 hr for eight days or until the fish dies. Thereafter the fish is monitored every 24 hr for a further month.

Agents can be administered simply by adding the agent to the media containing the fish. This approach has long been used to introduce anesthetics and other chemicals to fish embryos (Westerfield, 1993). Alternatively, agents can be microinjected into fish at the same site as cancerous cells, or elsewhere.

5. Assessment of Agent Activity

The activity of an agent against cancerous cells is its capacity to eliminate or reduce the number of injected cancerous cells, inhibit or eliminate their proliferation and/or inhibit or prevent their metastasis relative to contemporaneous or historical control animals receiving the same dose of cancerous cells without treatment. The fate of transplanted cancerous cells and their progeny can be monitored by immunostaining with an antibody specific to a cancer cell antigen not found in the recipient fish. Some types of cancerous cells can be distinguished visually from fish cells by virtue of the opaque nature of cancerous cells. Cancerous cells can also be labelled before or after transplantation. Suitable labels include fluorescent labels. Alternatively, cells can be labelled with dyes specifically taken up by cancerous cells. Monitoring is performed at intervals after administration of agent. For example, intervals of 24 hr are suitable. The pattern of stain indicates approximately the number of cells and their positions in the embryo. The number of cells is an indicator of proliferation. Changes in the location of cells, such as the disbursement of a cluster of cells over time, are an indicator of cell metastasis. Activity of an agent can be expressed as an EC50 meaning the dose of agent needed to achieve a desired endpoint of activity in 50% of treated fish. Examples of desired endpoints include elimination of cancerous cells, capacity significantly to inhibit the rate of proliferation of the cancerous cells, and capacity significantly to inhibit metastasis of the cancerous cells.

Agents can also be screened for capacity significantly to inhibit tumor-induced angiogenesis. After transplantation into fish, cancer cells secrete growth factors, such as VEGF, that promote new vessel growth in surrounding fish endothelial cells. Zebrafish are particularly suitable for analyzing angiogenesis because their transparent nature allows blood vessels to be directly visualized under a microscope. Procedures for monitoring angiogenesis in zebrafish are described in detail in WO 99/03852. Briefly, the host embryos are stained as follows: Embryos are fixed in 4% paraformaldehyde and stained for endogenous alkaline phosphatase activity. After fixation, embryos are treated with 100% methanol overnight at −20 degrees C. The embryos are rehydrated and equilibrated in NTMT buffer (0.1M Tris-HCl; 50 mM MgCl2; 0.1M NaCl; 0.1% Tween 20) at room temperature and then stained with 75 mg/ml NBT and 50 mg/ml X-phosphate. Optionally, expression profiles of tumor cells and fish cells can be determined before and after treatment with a potential anti-angiogenesis agent. A profile of differentially expressed genes is identified. Such a profile can be used for assays of drugs on other animals or human subjects in which new blood vessels are not so easily observable.

The above screening methods can be performed in parallel on multiple fish using a standard microplate well format, with a whole fish, typically at an embryonic stage, in one or more wells of the microplate. The format can be used to screen the same agent on multiple fish or to screen multiple agents on multiple fish. Both sample handling and detection procedures can be automated using commercially available instrumentation and software systems for rapid reproducible application of dyes and compounds and automated screening of target compounds.

6. Assessment of Side Effects

One of the difficulties associated with identifying compounds that can be used as anti-cancer therapeutics is that many of the compounds used to stop the proliferation of cancer cells also have deleterious effects on proliferating non-cancer cells. This is especially problematic when dealing with cancers that affect children, because many of their organs and tissues are still growing and developing. Side effects of agent administration on fish cells and/or embryogenesis can be monitored at intervals after administration of agent. Typically, measurements are performed at the same time as measurements to assess activity of administered agents.

Methods for analyzing necrotic tissue in fish are described in copending application WO 99/03852. Necrotic tissue can be detected by a variety of techniques, including, e.g., fluorescence microscopy, light microscopy, colorimetry, chemiluminescence, digital image analyzing, or standard microplate reader techniques. For example, fish embryos can be stained with a membrane-impermeant, nuclear-staining fluorescent dye, which permits detection of cell death activity (e.g., apoptosis or necrosis). Preferred dyes include those of the quinolium dye family, such as benzothiazolium-4-quinolium dyes (Molecular Probes), a number of which are commercially available. Benzothiazolium-4-quinolium cannot pass through intact membranes of cells of live embryos. However, this dye can enter dead or dying cells whose membranes have become discontinuous or disrupted (a characteristic of cells undergoing cell death, Liepins &. Bustamante, 1994)) intercalating into the DNA of the dead or dying cells. Upon intercalating into the DNA, the dye becomes intensely fluorescent, allowing for rapid detection of the labeled cells using simple fluorescent microscopy. The magnitude of the signal serves as a measure of the number of necrotic cells. The fluorescent dye is typically administered to the fish by adding the dye to the media containing the fish. Alternatively, the dye can be injected directly into the fish.

In addition to performing visual screens, specific molecular changes in fish tissues can be detected by in situ hybridization of RNA or antibody staining of specific proteins. In situ hybridization of mRNA is a routine molecular approach in fish (Westerfield, 1993). A digoxigenin-labeling kit from Boehringer Mannheim can be used to label the RNA probes. Whole mount in situ hybridization can be carried out as follows: embryos are fixed with 4% paraformaldehyde in PBS, lightly digested with proteinase K, and hybridized at 65° C. Alkaline phosphatase-conjugated anti-digoxigenin antibody is used to detect signals. After staining with NBT/X-phosphatase (Boehringer Mannheim), embryos are bleached in 100% methanol, refixed in 4% paraformaldyhyde, and stored in PBS. Multiple in situ hybridizations can be performed simultaneously on different fish in multiwell dishes.

A rapid staining procedure based on use of streptavidin (avidin) conjugated reporter enzyme, such as peroxidase, can be used to detect carboxilase enzymes in the liver of whole embryos. Such enzymes are naturally biotinylated. These biotinyl-lysine containing enzymes, such as Acetyl-CoA carboxylase and others carboxylases, are predominantly located in the liver. Since this group of enzymes are concentrated in the liver, staining is organ specific.

As an example, embryos (3, 4, 5 or 8 days old) were fixed with paraformaldahyde 1 hr at room temperature and treated with methanol 100% overnight at −20° C. The embryos were rehydrated with PBST and treated with bleaching solution ($H_2O_2$ 10%) for 20 minutes. After washing with PBST, the embryos were incubated in blocking solution (3% BSA, 100 mM NaCl in PBST). Embryos were incubated with streptavidin conjugated peroxidase (Pierce) (dilution 1:100 in blocking solution) with shaking at room temperature for two hours. They were then washed for twenty minutes three times with PBST and stained for peroxidase with diaminobenzidine (DBA) staining solution (1 ml of DBA stock solution [5 g of Diaminobezidine/l in PBS pH 7.4], 9 ml of PBS, 10 µl of $H_2O_2$ [30%]). Normally, specific liver staining is visualized in 1-5 minutes. Staining was stopped by several washes with water.

In addition a value for the Median Lethal Concentration (LC50), can be determined by administering serial dilutions of a compound and determining what proportion of fish die at each dilution. LC50 is the concentration needed to cause lethality in 50% of the embryos. Compounds, which exhibit a high Therapeutic Window (LC50/EC50), such as 100 or 1,000, are good potential drug candidates because toxicity at the therapeutic concentration is low.

7. Other Screening Assays

Closely analogous strategy and principles to those used for screening agents for activity against cancerous cells can be used to perform a variety of assays for agents on other cell types. For example, agents can be screened for cytotoxicity toward transplanted pathogenic cells, such as bacterial or fungal cells. Agents can also be screened for capacity to inhibit viral infection or pathogenesis of transplanted cells. In such methods, heterologous cells can be contacted with virus before or after transplant into fish. The virus is usually one that infects the transplanted heterologous cells without infecting the recipient fish. The method is particularly useful for propagating viruses that cannot replicate in culture, such as HBV, HCV and some strains of HPV (see, e.g., Rosen & Gretch, *Mol. Med. Today* 5, 393-399 (1999)). The methods are also useful for studying HIV and herpes viruses infection of transplanted human cells. Agents can be administered before or after introduction of virus to test for prophylactic and therapeutic activity respectively.

Agents can also be screened for activity in promoting cell differentiation and/or proliferation on normal cells. Although any of the types of agents described above can be used, growth factors, such as cytokines, GM-CF, EPO, FGF, PDGF, VEGF and stem cell factor are particularly suitable. A change in differentiation state is typically indicated by observing a change in a set of one or more differentiation markers. Such agents, once identified, have therapeutic value for promoting in situ repair of damaged or necrotic tissue or for promoting differentiation and/or propagation of cells in vitro for subsequent use in cell therapy or tissue engineering. Often, the cells used in such methods are stem cells, including totipotent stem cells, pluripotent stem cells and mesenchymal stem cells. For example, agents can be tested for activity in promoting differentiation of neural stem cells to neurons. Activity can be monitored from neural transduction or from differentiation markers of mature cells. Similarly, agents can be tested for activity in promoting differentiation of cardiac stem cells to myocytes, with activity being monitored by excitation level, capacity to beat or differentiation markers of mature cells.

Agents can also be screened for activity in promoting or inhibiting various functions of differentiated cells. Such functions include promoting expression or secretion of proteins. Agents identified as having such functions are useful in therapy for modulating expression of endogenous proteins or exogenous proteins whose coding sequences were introduced into a subject by gene therapy. For example, agents can be screened for capacity to promote secretion of insulin from islet cells. Alternatively, agents can be tested for capacity to promote expression of an exogenous enzyme introduced by genetic engineering into a human stem cells to be used in gene therapy.

8. Cell Therapy and Tissue Engineering Methods

Transplantation methods are also useful for culturing cells to be used in cell therapy or tissue engineering. Such methods are particularly useful for cells that cannot be propagated in vitro, or whose properties are adversely affected by in vitro propagation. In some methods, the fish serves as an incubator for propagation of transplanted cells allowing the cells to increase significantly in number without reaching a terminal differentiation state. Such cells are then recovered from the fish and introduced into a patient at the site at which tissue regeneration is needed. The cells then undergo further propagation and differentiation in situ in the recipient. Methods for ex vivo cell therapy are described by Mayhew et al., *Tissue Eng.* 4, 325-34 (1998); Wakitani et al., *Tissue Eng.* 4, 429-44 (1998). In other methods, propagation of the cells in the fish results in differentiation into a recognizable heterologous tissue type, such as a patch of skin. The heterologous tissue is then harvested from the fish and transplanted intact to a subject. For example, heterologous skin can be removed from a fish and used to replace a patch of damages or missing skin in a subject. Methods for skin transplantation are discussed by Mansbridge et al., *Tissue Eng* 4, 403-14 (1998). In other methods, heterologous cells are transformed with a nucleic acid sequence suitable for gene therapy. The heterologous cells are then introduced into fish for amplification prior to introduction into a patient. In other methods, hematopoietic human stem cells are introduced into fish for the large-scale production of human platelets and red blood cells, which can be harvested for treatment of patients. In other methods, human bone marrow cells are introduced into a fish for amplification, subsequent harvesting and use in autologous or allogeneic bone marrow transplantation. Other applications of such methods include production of scaffolds for tissue engineering, production of cartilage, hart valves, bone repair, ligament repair, menischal implants, autologous chondrocyte transplantation, nerve regeneration vasculogenesis, and propagation of pancreatic, hepatic or glial cells.

9. Other Therapeutic Methods

In some methods, the fish provides an incubator to propagate cancerous cells for subsequent use as a vaccine. In such methods, cancerous cells are obtained from a patient biopsy, transplanted into a fish, and propagated. The propagated cells, which are considerably increased in number relative to the transplanted cells, are then harvested. The harvested cells are then killed and reintroduced into the patient. The killed cells bear tumor antigens that stimulate an immune response against live cancer cells remaining in the patient (see e.g., Eck et al., *Cancer Immunol. Immunother.* 6, 336-41 (1999); Carr-Brendel et al., *J. Immunother.* 22, 415-22 (1999)). Harvested cells can also be used as an immunogen into a laboratory animal to generate antibodies for passive immunotherapy in the patient.

In other methods, mixed populations of cancerous and noncancerous cells are obtained from a patient. The cells are separated into clonal isolates, and different clonal isolates introduced into different fish. The cells are then propagated in the fish. After propagation, cells are screened for presence of a cancer specific antigen. Cells lacking such an antigen are recovered from their host fish and retransplanted into the patient from whom they were obtained. Such methods are particularly useful for distinguishing cancerous and noncancerous cells in bone marrow transplant patients.

10. Diagnostic Methods

The present methods can also be used for diagnosis of biopsies from subjects. Biopsied cells are transplanted into a fish and monitored as described in Section II, particularly for proliferation and/or metastasis. Proliferation and/or metastasis of transplanted cells is an indication that the biopsy contains cancerous cells. The rate or proliferation and/or metastasis is an indicator of the malignancy of the tumor and the prognosis of the patient. Transplanted cells can also be screened with various antineoplastic treatments, such as radiation and chemotherapy, to determine which treatment is most appropriate for cancerous cells in a particular patient. Using this bioassay, the clonogenic potential of residual lymphoma cells in bone marrow, peripheral blood and body fluids can be determined. Analogous methods can be used to detect cellular or viral pathogens in tissue samples from patients. Culturing cells within the recipient fish provides amplification by which the pathogen is more easily detected. Such methods are particularly useful for analyzing biopsies from patients having received transplanted tissue (see e.g., Cohen et al., *Pediatr. Transplatn.* 3, 322-7 (1999); Carman et al., *J. Heptatol.* 2, 195-201 (August 1999).

11. Research Applications

Transplanting cells into fish also has a number of fundamental research application. For example, the methods can be used to monitor differentiation of a cell lineage in isolation of other cell types from the same organisms. Such can be achieved by transplanting nonterminally differentiated cells into a population of fish, and then monitoring markers of differentiation in the transplanted cells and/or in the host fish over time. Arrays containing probes complementary to mRNA provides a suitable means for monitoring (see, e.g., WO 97/10365). By appropriate selection of probes, it is possible to distinguish fish mRNA from those of transplanted cells in the same mixture of mRNA. Alternatively, micro tissue manipulation can be used to prepare separate tissue samples from heterologous cells and host cells. Such expression patterns are themselves useful as in drug screening assays. For example, if a particular pattern is determined to be characteristic of a particular differentiation state, that pattern can be used as an end point in screening agents for capacity to inhibit or promote differentiation.

EXAMPLE 1

Transplantation of HEP2 Cells

To test the feasibility of transplanting human cells in zebrafish embryos, we transplanted cells derived from human cancer tissue: HepG2 cells (ATCC HB-8065) derived from a human hepatoblastoma which have previously been shown to form lethal tumors when injected into nude mice ((Wenger et al., 1995; Chin et al., 1997)). In addition to forming tumors, HepG2 cells also secret a number of factors which are present in normal liver cells including the vessel inducing protein, VEGF. This made it possible to assay the viability of the HepG2 cells by looking for effects of VEGF including increased vessel formation and heart defects (Drake & Little, 1995; Feucht et al., 1997) of HepG2 cells both by watching the tumors grow and by using vital stains that identify dead and dying cells. In addition, we could identify the HepG2 cells both by their visual appearance and by using specific antibodies that recognize human but not zebrafish antigens.

A. Materials and Methods

1. Cell Culture

HepG2 cells were maintained as indicated in American Type Culture Collection (ATCC) procedures. Briefly, the cells were cultivated in MEM (Minimum Essential Media) (Gibco) supplemented with glutamine, essential amino acids and pyruvate. The cells were grown to 80% confluence and harvested by adding trypsin/EDTA, washed twice with the same culture media, and resuspended in PBS immediately before injection.

2. Transplantation

The transplantation technique used is similar to that described by Ho & Kane, 1990. Briefly, after cells had been resuspended in PBS, the cells were backfilled into a pulled glass micropipet with a tip diameter of 15 micron i.d. and 18 micron o.d. This permits easy penetration of the embryo and injection of intact cells. The micropipet was attached to a micromanipulator and an air-driven Cell Tram (Eppendorf). Using the micromanipulator, the tip of the micropipet was inserted into the embryo and 10-50 cells were expelled from the tip using positive pressure from the Cell Tram. Transplantations were carried out in three different regions of the embryo (FIG. 6):

1) into the animal portion of the embryo without a priori knowledge of the position of the transplanted cells in the hosts;
2) into random positions in the yolk cell and;
3) into the margin between the embryo and the yolk ball.

In addition, two types of transplantations were carried out: a) single site transplantations; and b) multiple site injections, in which the cells were disbursed throughout the tissue instead of clumped together. All transplantations were performed at or near the high stage (1000-2000 cells) of development.

3. Embryo Handling

Embryos were generated by natural matings between wild type adult fish. Prior to injection, 4-8 cell stage embryos are treated with protease (1 mg/ml of embryo media) for 5 minutes to remove the chorions. The embryos were then washed 5 times in embryo media to remove both the protease and the digested chorions. The embryos were then allowed to recover in a glass beaker for several hours in embryo media at 27° C. until they reached the high stage of development. The embryos were then placed in a holding well made from 1% agarose in embryo media. 30-40 embryos were lined up side by side and oriented. Following the transplantation, the embryos were removed from the holding tray and placed into agar-coated culture plates and allowed to recover. After 24 hours, the embryos were transferred to new culture plates and maintained in fish water (Santa Cruz Technology) for the duration of the experiment.

4. Cell Labelling

Before harvesting, cells were incubated in a DiI-Labelling solution (0.05% diI in 0.3M sucrose) for 15 min. DiI is a lipophilic carbocyanine trace (Molecular Probes) used in a variety of long-term cell tracking applications, including transplantation migration studies (Serbedzija et al., 1992). Using epifluorescence microscopy, DiI-labelling was visualized in both individual transplanted cells as well as in cell masses.

5. Antibody Detection of Transplanted Cells

The HepG2 transplanted cells were immunodetected using an anti-human keratinocyte 18 antibody (REF). Cytokeratin 18 is an intermediate filament protein, which has been shown to be expressed in HepG2 under a variety of conditions (Cruickshank et al., J. Hepatol. 29, 550-8 (1998). Transplanted embryos were fixed with paraformaldehyde 1 hr at room temperature and treated with methanol 100% overnight at −20° C. The embryos were rehydrated with PBST (0.1% Tween 20 in PBS) and treated with bleaching solution ($H_2O_2$ 10%) for 20 minutes. After washing with PBST, the embryos were incubated in blocking solution (20% Inactivated Calf Serum, 1% DMSO in PBST) for one hour at room temperature and shaking. The first antibody, monoclonal mouse IgG anti-human keratinocyte 18 (Santa Cruz Technology), was then added (dilution 1:2000) and incubated for two hours at room temperature with shaking. Four washes with the same blocking solution were performed and then the second antibody, rabbit anti-mouse IgG conjugated with alkaline phosphatase, was added (dilution 1:2000) and incubated for two hours at room temperature with shaking. The embryos were washed twice with the same blocking solution and finally equilibrated in NTMT solution (50 mM $MgCl_2$, 100 mM NaCl, 100 mM Tris/HCl pH 9.5). Finally, the embryos were stained for alkaline phosphatase using NBT/BCIP and visualized by light microscopy.

6. Vessel Staining

Embryos were fixed in 4% paraformaldehyde and stained for endogenous alkaline phosphatase activity. After fixation, embryos will be permeabilized in acetone at −20° C., equilibrated in NTMT buffer (0.1M Tris-HCl; 50 mM MgCl; 0.1M NaCl; 0.1% Tween 20) at room temperature and then stained with 75 mg/ml NBT and 50 mg/ml X-phosphate.

7. Western Blot Analysis

Dechorionated embryos were resuspended in 1×SDS gel loading buffer, boiled for 2 minutes, and centrifuged for 10 minutes at 14,000 rpm. The supernatant samples were then loaded on a 10% SDS-polyacrylamide gel. Kaleidoscope prestained proteins (Bio-Rad) were used as standards. After electrophoresis, the proteins were transferred to a nitrocellulose membrane (BA85, Schleicher & Schuell), during 4 hours at 4° C. using 120-200 mA. The filters were blocked overnight in TBST (10 mM Tris/HCl pH 8.0, 150 mM NaCl, 0.05% Tween 20) with 5% milk. Then, the filters were incubated with the first antibody (monoclonal mouse IgG anti-human Keratinocyte 18, Santa Cruz Technology, dilution 1:2000) for 30 minutes at room temperature with shaking. Four washes with the same blocking solution were performed and then the second antibody (rabbit anti-mouse IgG conjugated with alkaline phosphatase, dilution 1:2000) were added and incubated for two hours at room temperature with shaking. The anti-Keratinocyte 18 binding reaction was visualized using One Step TMB Blotting (3,3'-5,5' tetra-methyl-benzidine) (Pierce).

8. Antibody Staining

Embryos were collected 24 hr after transplantation and stained with mouse IgG anti-human keratinocyte 18 monoclonal antibody which recognizes HepG2 cells but does not bind to any endogenous fish antigens. Using this antibody, we were able to detect labeled cells in both the embryonic tissue and the yolk. We further observed that these cells were often adjacent to sites of morphological defects presumed to be induced by the transplanted cells.

9. BRDU Labelling 5-bromo-2'- deoxyuridine (BrdU) is a mitotic S-phase marker. To assay for proliferation, a 3 µM solution of BrdU (Sigma) was injected into 24 hour xenograft zebrafish embryos in which cells had previously been transplanted. Embryos were incubated for 24 hours to permit incorporation of BrdU into the DNA of the transplanted cells and the host cells. Embryos were then collected, fixed with 4% PFA at room temperature, and dehydrated to 100% methanol.

B. Results

80% of the 357 embryos injected with cells survived 24 hrs after injection. The opaque HepG2 cells were observed in approximately 10% of the surviving animals. There was no obvious correlation between the location of the injection and subsequent observation of cells in the embryo. Twenty-four hours after transplantation, embryos in which the HepG2 cells were visible could be divided into three distinct groups:

1. embryos which looked normal, but which had large cell masses in the yolk (FIG. 1),
2. embryos which looked normal, but had individual cells in the body (FIG. 2), and
3. embryos which had morphological defects and a large mass of cells (FIG. 3).

Both groups 1 and 3 evidence examples of the tumor forming ability of the HepG2 cells. In both cases, the observed cell masses became larger with time, suggesting that the HepG2 cells were proliferating. In addition, when the masses are in the body of the embryo, we often observed a teratogenic effect on the embryos that could not be explained solely by the mechanical presence of the cell mass (FIG. 4). This suggests that the HepG2 cells are secreting factors which effect the embryo. In addition, we often observed zebrafish cells incorporated into the cell mass (FIG. 5).*suggesting* that the HepG2 cells may be transforming the zebrafish cells. The second group also suggests that the HepG2 cells can metastasize in the fish embryo. In several instances, embryos with large masses of HepG2 cells died 48-72 hrs after transplantation. In contrast, embryos with small masses or scattered individual cells survived 7 days, at which time the experiment was ended.

In embryos, (zebrafish or other species) exogenous VEGF, which is known to be secreted by HepG2 cells, causes both increased vessel formation and heart defects (Drake & Little, 1995; Feucht et al., 1997). Both of these phenomenon were observed in embryos which had visible HepG2 cell masses. FIG. 5 shows an embryo in which the HepG2 cells were present in the pericardium. The heart is clearly malformed. Endogenous alkaline phosphatase staining of embryos having large cell masses in the yolk for vessel formation showed extensive outgrowth of blood vessels in and around the yolk, where they are not normally observed. We also observed a thickening of the large vessels, including the dorsal aorta and ventral vein.

To confirm that the transplanted HepG2 cells were viable, we examined xenograft embryos for the presence of human VEGF (hVEGF) and human AFP (hAFP), two proteins normally secreted by HepG2 cells in culture and to be present in the blood of patients diagnosed with hepatocellular carcinoma (Huber, 1985; Eraiser et al. 1998; Louha et al., 1997). High levels of hVEGF have also been correlated with adverse effects on heart development in zebrafish and other vertebrates (Drake, et al., 1995; Feucht, et al., 1997, Serbedzija, 1999). For these experiments, xenograft embryos were stained with human specific antibodies to either hVEGF or hAFP and these antibodies were detected using RPE labeled secondary antibodies. Because the fluorescence spectra of Dii and RPE are similar, transplantations were performed using unlabeled HepG2 cells. Embryos were collected 24 to 72 hours after transplantation. Transplanted cells exhibit appropriate cell characteristics including the production of proteins. 100% of the embryos stained for VEGF (100) contained labelled cells in cell masses. In addition, in 50% of hVEGF positive embryos, individual RPE-labeled cells were detected in close proximity to the cell mass. As was shown with hVEGF staining, 100% of the embryos stained for hAFP had labeled cells in the cell masses (FIG. 5). In contrast to hVEGF staining, in hAFP positive embryos, no cells were observed outside the cell mass, regardless of when the embryos were collected. For both hVEGF and hAFP antibodies, staining was restricted to HepG2 cells. Neither hVEGF nor hAFP label was observed in non-xenograft control embryos. Claim 61 was canceled.

To assay for proliferation, a 3 µM solution of BrdU (Sigma) was injected into 24 hour xenograft zebrafish embryos in which cells had previously been transplanted. Embryos were incubated for 24 hours to permit incorporation of BrdU into the DNA of the transplanted cells and the host cells. Embryos were then collected, fixed with 4% PFA at room temperature, and dehydrated to 100% methanol. Anti-BrdU and Ant-CK18 Double Labeling: To identify HepG2 cells that had incorporated BrdU, embryos were double stained using antibodies against BrdU and CK18. The protocol was similar to the antibody protocol described above, with the following modifications: 1) prior to incubating in blocking solution, BrdU-labeled embryos were immersed in 2N Hydrochloric Acid for 30 minutes to increase the accessibility of the DNA to the antibody; 2) following incubation with the anti-CK18 and its RPE-conjugated secondary antibody, embryos were incubated with a FITC-conjugated monoclonal antibody to BrdU (Sigma). The antibodies were then visualized using an epifluorescence microscope.

All proliferating cells, including both the transplanted cells and the host cells, were labeled. Specifically to identify proliferating HepG2 cells, we performed a double labeling experiment using human specific anti-CK18 antibody. We detected BrdU and anti-CK18 using an FITC-conjugated secondary antibody and an RPE-conjugated secondary antibody, respectively. As described previously, transplantations were carried out using unlabeled HepG2 cells. 100 xenograft embryos in which HepG2 cell masses were visible were collected 24 hours after transplantation. A 3 µM solution of BrdU was then injected into the yolkball of 80 of the xenograft embryos. The embryos were then allowed to develop for an additional 24 hours before fixation and staining. Although the anti-BrdU antibody labeled both HepG2 cells and host cells, only HepG2 cells were labeled by both antibodies (FIG. 7, panels A-C). After BrdU injection, 72 of the 80 xenograft embryos contained cells labeled with both antibodies. In contrast, the control xenograft embryos, which were not injected with BrdU, contained only anti-CK-18 labeled cells. This experiment clearly shows that transplanted HepG2 cells proliferate in the zebrafish embryo. HepG2 cell masses in zebrafish embryo are histologically similar to xenograft HepG2 tumors in adult mice. To determine if the HepG2 cell masses were morphologically similar to tumors generated in the mouse models and their human counterparts, we performed a histologic examination of the xenograft embryos collected 24 and 48 hours post transplantation. Although the cell masses in the zebrafish embryo were smaller (100-300 µm in diameter) than tumors observed in mice (7-10 mm; Vucenik, et al., 1998), the general morphology of HepG2 cells in cell masses was similar (Klein, et al., 1989). Specifically, the HepG2 cells were round and had little cytoplasm (FIG. 8 panels A-C). The HepG2 cells were easily identifiable in tissue sections because the nuclei of the HepG2 cells were larger and more compact than the nuclei of zebrafish cells. In contrast to the host cells, the HepG2 cells were tightly packed with little or no extracellular space between cells. Cells with smaller nuclei, presumed to be zebrafish cells, were also present in the HepG2 cell masses. There was no evidence of vacuolated space in any of the cell masses, which would suggest that the transplanted cells were dying.

To confirm metastasis, we transplanted labeled cells that can be tracked over several days. Prior to transplantation, the HepG2 cells were labelled with DiI and then harvested by adding trypsin/EDTA, washed twice with culture media, and resuspended in PBS before transplantation into the host embryo. 24 hours after transplantation, host embryos were screened to identify those that had a single mass of labeled cells. We continued to observe these embryos, checking for cells that left the mass and disseminated to other regions of the embryo. To confirm that the labeled cells were HepG2 cells, we stained the embryos with anti-Cytokeratin 18 antibody. We transplanted 100 embryos; at 24 hours of development, all 95 of the surviving embryos contained labeled cell masses. Next, 24 embryos that contained a single, cohesive mass of labeled cells were selected for continued observation. At 48 hours of development, 22/24 embryos contained DiI labeled cells outside the original cell mass (FIG. 9); at 72 hours of development, all 22 embryos contained individual DiI labeled cells associated with the vasculature. Specifically, individual cells were found: 1) in the tail mesenchyme adjacent to the dorsal vessel and/or the axial vein, 2) throughout the head adjacent to the cranial vessels; and 3) within the wall of the heart in either the myocardium or the endocardium. By 6 days, new cell masses were observed in the tail (FIG. 9) and head, indicating that individual labeled HepG2 cells, observed in those locations at earlier time points, were proliferating.

C. Conclusion

The above experiment shows that conventional wisdom that human cancer cells cannot survive at the growth temperature of zebrafish (i.e., 27° C. in the present application) is incorrect. Moreover, cells appear not only to survive, but to form masses which may be similar to the tumor formed when HepG2 are injected into nude mice. In addition, some tumor cells appear to metastasize in the zebrafish embryo. Thus, zebrafish can be used to screen agents for activity against human cancer cells.

EXAMPLE 2

Transplantation with Other Human Cell Lines and Human Tumor Cells

Several other human cell types have been transplanted into zebrafish using the same methods described for HEP-2 cells. The results are summarized in Table 1.

TABLE 1

Summary of xenografts with various cell lines

| Cell Line | Type | Cell Mass Formation | Cell Mass Growth | Morphological Characteristics | Teratogenic Effects | Lethality |
|---|---|---|---|---|---|---|
| HepG2 | Hepatocellular carcinoma | Yes | Yes | Compacted masses located throughout the embryo | ~5% | 2-7 days |
| CCCL-18 | Colon cancer | Yes | Yes | Compacted masses located throughout the embryo | ~5% | 2-7 days |
| NT2D | Embryonic teratocarcinoma | Yes | No | Loosely clustered cell in the CNS; Cells dispersed during embryonic growth | % | None observed |
| JK | Lymphoma | Yes | Yes | Cells clustered in head | | 3 days |
| Mac-1 | Lymphoma | Yes | Yes | Cells in head and tail | | 3-4 days |

TABLE 1-continued

Summary of xenografts with various cell lines

| Cell Line | Type | Cell Mass Formation | Cell Mass Growth | Morphological Characteristics | Teratogenic Effects | Lethality |
|---|---|---|---|---|---|---|
| Mac-2a | Lymphoma | Yes | Yes | Cells in head and tail | | na |
| CII-37 from human biopsy | Lymphoma/ Block of apoptosis | No | No | Cell did not divide but were present in CNS and tail | | Still alive at 7 days |
| TMP Tumor from xenograft mouse | Lymphoma | Yes | Yes | Cell mass formed and cells were present in the circulation | | Still alive at 7 days |

All properties were determined by microscopic observation. Presence of cell mass indicates some proliferation of transplanted cells. Cell mass growth indicates more extensive proliferation. Presence of transplanted cells throughout the embryo as is the case for HepG2 and CCL-18 cells is indicative of metastasis. Presence of NT2D cells, a neural stem cells, in the CNS indicates that transplanted cells respond to endogenous signalling from within the recipient fish.

From the foregoing, it should be apparent that the invention includes a number of uses that can be expressed concisely as follows. The invention includes the use of a fish as a recipient to maintain viability of and/or propagate heterologous cells. The invention further includes the use of heterologous cells introduced into a fish to screen a potential drug for a response of the cells. The invention further includes the use of heterologous cells introduced into a fish for the manufacture of a medicament for treatment of a patient. The invention further includes the use of heterologous cells transplanted into a fish for diagnosis of a pathogen or cancerous cell within a patient tissue sample. While the foregoing invention has been described in some detail for purposes of clarity and understanding, it will be clear to one skilled in the art from a reading of this disclosure that various changes in form and detail can be made without departing from the true scope of the invention. The above examples are provided to illustrate the invention, but not to limit its scope; other variants of the invention will be readily apparent to those of ordinary skill in the and are encompassed by the claims of the invention. The scope of the invention should, therefore, be determined not with reference to the above description, but instead should be determined with reference to the appended claims along with their full scope of equivalents. All publications, references, and patent documents cited in this application are incorporated by reference in their entirety for all purposes to the same extent as if each individual publication or patent document were so individually denoted.

REFERENCES

Chen and Fishman (1996) *Development* 123:293-302.
Chin, Kurashima, Ogura, Tajiri, Yoshida and Esumi (1997) *Oncogene* 24; 15(4):437-42.
Drake and Little (1995) *Proc Natl Acad Sci USA* 15;92(17): 7657-61.
Feucht, Christ and Wilting (1997) *Am J Pathol* 1997 November;151(5):1407-16.
Granato and Nusselien-Volhard (1996) *Cur. Op. Gen. Dev.* 6:461-468.
Greiner, Hesselton and Shultz (1998) *Stem Cells* 16(3):166-177.
Hammerschmidt, Serbedzija and McMahon (1996) *Genes and Devel.* 10:2452-2461.
Ho and Kane (1990) *Nature* 348:728-730.
Katsanis, Weisdorf and Miller (1998) *Bone Marrow Trans.* 22(2):185-91.
Liepins and Bustamante (1991) *Scanning Micrcosc.* 8:631-641.
Stainier and Fishman (1994) *Trends Cardiovasc. Med.* 4:207-212.
Weinstein, Stemple, Dreiver and Fishman (1995) *Nature Med.* 1:1143-1147.
Wenger, Rolfs, Marti, Baucr and Gassmann (1995) *J Biol Chem* 17;270(46):27865-70.
Westerfield (1993) In: The Zebrafish Book.
Wylie (1996) *Development* 123:1-481.
Yang, Tang, Zhang, Cheng and Mack (1997) *Cancer Letters* 117:93-98.

What is claimed is:

1. A method of analyzing a sample for presence of a cancer cell or pathogen, comprising:
   (a) obtaining a sample from a patient containing a cell or population of cells;
   (b) introducing the cell or the population of cells into a zebrafish embryo that has not yet developed an immune system that would subject the cell or population of cells to immune rejection; and
   (c) detecting a property of the cell or the population of cells to indicate whether the cell or the population of cells comprises a cancer cell or pathogen.

2. The method of claim 1, wherein the sample is obtained from bone marrow, peripheral blood, a body fluid or a transplanted tissue.

3. The method of claim 1, wherein the sample is from a biopsy.

4. The method of claim 1, wherein the cell or the population of cells is a human cell or a population of human cells.

5. The method of claim 1, wherein introducing comprises microinjecting the cell or the population of cells into the zebrafish embryo.

6. The method of claim 1, wherein the cell or the population of cells are microinjected into a blastula stage embryo.

7. The method of claim 1, wherein the cell or the population of cells are microinjected into the yolk of the zebrafish embryo.

8. The method of claim 1, wherein a population of cells are introduced into the zebrafish embryo.

9. The method of claim 8, further comprising culturing the zebrafish embryo after the population of cells is introduced, whereby cancer cells present in the cell population proliferate.

10. The method of claim 8, further comprising culturing the zebrafish embryo after the population of cells is introduced, whereby a pathogen present in the cell population is amplified.

11. The method of claim 8, wherein the property detected is cell proliferation or metastasis, detection of proliferation or metastasis being an indication that the population of cells contains cancer cells.

12. The method of claim 8, wherein the property detected is the rate of cell proliferation or metastasis.

13. The method of claim 11, wherein cell proliferation is detected by immunostaining with an antibody specific for cancer cells.

14. The method of claim 11, wherein metastasis is detected by detecting movement of cells from the cell population relative to an initial site at which the cell population was introduced.

15. The method of claim 1, wherein the pathogen is a bacterium, a virus or a fungus.

* * * * *